（12）United States Patent  
Sethuraman et al.

(10) Patent No.: US 8,137,954 B2  
(45) Date of Patent: Mar. 20, 2012

(54) ERYTHROPOIETIN COMPOSITIONS

(75) Inventors: Natarajan Sethuraman, Hanover, NH (US); Juergen Nett, Grantham, NH (US); Robert Davidson, Enfield, NH (US)

(73) Assignee: Glycofi, Inc., Lebanon, NH (US)

( * ) Notice: Subject to any disclaimer, the term of this patent is extended or adjusted under 35 U.S.C. 154(b) by 0 days.

(21) Appl. No.: 12/779,171

(22) Filed: May 13, 2010

(65) Prior Publication Data

US 2011/0086798 A1   Apr. 14, 2011

Related U.S. Application Data

(62) Division of application No. 11/804,510, filed on May 18, 2007, now Pat. No. 7,851,438.

(60) Provisional application No. 60/801,688, filed on May 19, 2006, provisional application No. 60/905,770, filed on Mar. 7, 2007.

(51) Int. Cl.
  *C12N 1/00* (2006.01)
  *C12N 15/09* (2006.01)
  *C12N 15/74* (2006.01)
  *C12N 15/00* (2006.01)
  *C12P 1/02* (2006.01)
  *C12P 21/04* (2006.01)

(52) U.S. Cl. ............. 435/254.21; 435/69.4; 435/171; 435/71.1; 435/69.6; 435/483; 435/455

(58) Field of Classification Search .................. None
See application file for complete search history.

(56) References Cited

U.S. PATENT DOCUMENTS

| | | | |
|---|---|---|---|
| 4,835,260 A | 5/1989 | Shoemaker | |
| 5,641,663 A | 6/1997 | Garvin et al. | |
| 7,029,872 B2 * | 4/2006 | Gerngross | 435/69.1 |
| 7,326,681 B2 | 2/2008 | Gerngross | |
| 7,332,299 B2 | 2/2008 | Hamilton | |
| 7,405,198 B2 * | 7/2008 | DeFrees et al. | 514/1.3 |
| 7,449,308 B2 | 11/2008 | Gerngross et al. | |
| 2004/0018590 A1 | 1/2004 | Gerngross et al. | |
| 2007/0037248 A1 * | 2/2007 | Bobrowicz et al. | 435/69.1 |

FOREIGN PATENT DOCUMENTS

| | | |
|---|---|---|
| EP | 0154316 B1 | 3/1985 |
| EP | 0315456 B1 | 11/1988 |
| EP | 0401384 B1 | 12/1989 |
| WO | 9402611 | 2/1994 |
| WO | 9424160 | 10/1994 |
| WO | 9425055 | 11/1994 |
| WO | 9505465 | 2/1995 |
| WO | 9605309 | 2/1996 |
| WO | 9611953 | 4/1996 |
| WO | 0032772 A3 | 6/2000 |
| WO | 2004033651 A2 | 4/2004 |
| WO | 2004074458 A2 | 9/2004 |

OTHER PUBLICATIONS

Takeuchi et al. 1988. J. Biol. Chem. 263:3657-3663.*
Bernaudin et al., "Potential Role for Erythropoietin in Focal Permanent Cerebral Ischemia in Mice", Journal of Cerebral Blood Flow & Metabolism, vol. 19, pp. 643-651 (1999).
Briggs et al., "Hepatic clearance of intact and desialylated erythropoietin", Americal Journal of Physiology, vol. 227, No. 6, pp. 1385-1388 (1974).
Broudy et al., "Recombinant Human Erythropoietin: Purification and Analysis of Carbohydrate Linkage", Archives of Biochemistry and Biophysics, vol. 265, No. 2, pp. 329-336, (1988).
Caldas et al., "Design and systhesis of germline-based hemi-humanized single-chain Fv against the CD18 surface antigen", Protein Engineering, vol. 13, No. 5, pp. 353-360, (2000).
Celik et al., "Erythropoietin prevents motor neuron apoptosis and neurologic disability in experimental spinal cord ischemic injury", PNAS, vol. 99, No. 4, pp. 2258-2263 (2002).
Danna et al., "Erythoropoietin Therapy for the Anemia Associated with AIDS and AIDS Therapy and Cancer", ed. Erythropoietin in Clinical Applications—An Internationl Perspective, N.Y., NY, Marcel Dekker, Inc. pp. 301-324 (1990).
Deininger et al., "Galectin-3 Labeling Correlates Positively in Tumor Cells and Negatively in Endothelial Cells with Malignancy and Poor Progonosis in Oligodendroglioma Patients", Anticancer Research 22, pp. 1585-1592 (2002).
Dordal et al., The Role of Carbohydrate in Erythropoietin Action:, Endocrinology, vol. 116, No. 6, pp. 2293-2299 (1985).
Dube et al., "Glycosylation at Specific Sites of Erythropoietin Is Essential for Biosynthesis, Secretion, and Biological Function", The Journal of Biological Chemistry, vol. 263, No. 33, pp. 17516-17521 (1988).
Egrie et al., "Characterization and Biological Effects of Recombinant Human Erythropoietin", Immunobiol, vol. 172, pp. 213-224 (1986).
Francis et al., "PEGylation of cytokines and other therapeutic proteins and peptides: the importance of biological optimisation of coupling techniques", Internationl Journal of Hematology 68, pp. 1-18 (1998).
Fukuda et al., "Survival of Recombinant Erythropoietin in the Circulation: The Role of Carbohydrates", Blood, vol. 73, No. 1, pp. 84-89 (1989).
Ashwell G. and Kawasaki T., "A Protein from Mammalian Liver that Specifically Binds Galactose-Terminated Glycoproteins", Methods in Enzymology 50, Complex Carbohydrates, Mammalian-Binding Protein, pp. 287-288 (1978).
Goldwasser et al., "On the Mechanism of Erythropoietin-induced Differentiation", The Journal of Biological Chemistry, vol. 249, No. 13., p. 4202-4206 (1974).
Hamilton, et al, "Humanization of Yeast to Produce Complex Terminally Sialylated Glycoproteins", Science, vol. 313, pp. 1441-1443 (2006).
Higuchi et al., "Role of Sugar Chains in the Expression of the Biological Activity of Human Erythropoietin", The Journal of Biological Chemistry, vol. 267, No. 11, pp. 7703-7709 (1992).

(Continued)

*Primary Examiner* — Shulamith H Shafer

(57) ABSTRACT

Methods and materials are provided for the production of compositions of erythropoietin protein, wherein said compositions comprise a pre-selected N-linked glycosylation pattern as the predominant N-glycoform.

10 Claims, 32 Drawing Sheets

OTHER PUBLICATIONS

Junk et al., "Erythropoietin administration protects retinal neurons from acute ischemia-reperfusion injury", PNAS, vol. 99, No. 16, pp. 10659-10664 (2002).

Lai et al., "Structural Characterization of Human Erythropoietin", The Journal of Biological Chemistry, vol. 261, No. 7, pp. 3116-3121 (1986).

Lee-Huang et al., "Cloning and expression of human erythropoietin cDNA in *Escherichia coli*", Proc. Natl, Acad. Sci. USA, vol. 81, pp. 2708-2712 (1984).

Marks et al., "Human Antibodies from V-gene Libraries Displayed on Phage", J. Mol. Biol. 222, pp. 581-597 (1991).

Morell et al., "Physical and Chemical Studies on Ceruloplasmin", The Journal of Biological Chemistry, vol. 243, No. 1, pp. 155-159 (1968).

Restelli et al., "The Effect of Dissolved Oxygen on the Production and the Glycosylation Profile of Recombinant Human Erythropoietin Produced From CHO Cells", Biotechnology and Bioengineering, vol. 94, No. 3, pp. 481-494 (2006).

Sasaki et al., "Carbohydrate Structure of Erythropoietin Expressed in Chinese Hamster Ovary Cells by a Human Erythropoietin cDNA", The Journal of Biological Chemistry, vol. 262, No. 25, pp. 12059-12076, (1987).

Yamaguchi et al, "Effects of Site-directed Removal of N-Glycosylation Sites in Human Erythropoietin on Its Production and Biological Properties", The Journal of Biological Chemistry, vol. 266, No. 30, pp. 20434-20439 (1991).

Lowy et al, "Inactivation of Erythropoietin by Neuraminidase and by Mild Substitution Reactions", Nature 185, pp. 102-103 (1960).

Hamilton et al, "Production of Complex Human Glycoproteins in Yeast", Science, vol. 301, pp. 1244-1246 (2003).

Takeuchi et al., "Role of Sugar Chains in the in Vigtro Biological Activity of Human Erythropoietin Produced in Recombinant Chinese Hamster Ovary Cells", The Journal of Biological Chemistry, vol. 265, No. 21, pp. 12127-12130 (1990).

Wen et al., "Erythropoietin Structure-Function Relationshops: High Degreee of Sequence Homology Among Mammals", Blood, vol. 82, No. 5, pp. 1507-1516, (1993).

Roberts, MJ et al., "Chemistry for Peptide and ProteinPEGylation", Advanced Drug Delivery Reviews, vol. 54, pp. 459-476 (2002).

* cited by examiner

YGLY1461
[ura5Δ::MET16 och1Δ::lacZ bmt2Δ::lacZ/KlMNN2-2
mnn4L1Δ::lacZ/MmSLC35A3 Δpno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8]

pGLY165 ↓

YGLY1703
[ura5Δ::MET16 och1Δ::lacZ bmt2Δ::lacZ/KlMNN2-2
mnn4L1Δ::lacZ/MmSLC35A3 Δpno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ-URA5-lacZ/TrMDS1]

pGLY2088 ↓

YGLY2849
[ura5Δ::MET16 och1Δ::lacZ bmt2Δ::lacZ/KlMNN2-2
mnn4L1Δ::lacZ/MmSLC35A3 Δpno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ-URA5-lacZ/TrMDS1
AOX1:Sh ble/AOX1p/ScαMFpre-GFI800 ]

pGLY2456 ↓

YGLY3159
[ura5Δ::MET16 och1Δ::lacZ bmt2Δ::lacZ/KlMNN2-2
mnn4L1Δ::lacZ/MmSLC35A3 Δpno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ-URA5-lacZ/TrMDS1
AOX1:Sh ble/AOX1p/ScαMFpre-GFI800
TRP2::ARG1/MmCST/HsGNE/HsCSS/HsSPS/MmST6-33]

FIG. 1D

SDS-PAGE Coomassie Stain of Purified EPO

ERYTHROPOIETIN COMPOSITIONS

RELATED APPLICATIONS

The present application is a divisional application of U.S. Ser. No. 11/804,510, filed May 18, 2007, now U.S. Pat. No. 7,851,438, which claims priority to provisional applications U.S. Ser. No. 60/801,688, filed May 19, 2006 and U.S. Ser. No. 60/905,770, filed Mar. 7, 2007, each of which are hereby incorporated by reference herein.

REFERENCE TO SEQUENCE LISTING SUBMITTED ELECTRONICALLY

The sequence listing of the present application is submitted electronically via EFS-Web as an ASCII formatted sequence listing with a file name GFIBIO22376USDIV_SEQTXT_13MAY2010.TXT", creation date of May 13, 2010, and a size of 3 KB. This sequence listing submitted via EFS-Web is part of the specification and is herein incorporated by reference in its entirety.

FIELD OF THE INVENTION

The present invention relates to the field of molecular biology, in particular the invention provides materials and methods for the production of homogeneous compositions of PEGylated erythropoietin with desired N-glycoforms.

BACKGROUND OF THE INVENTION

The production of recombinant glycoproteins has been an area of great activity for the biotechnology industry. One drawback of recombinant glycoproteins has been the heterogeneity of glycosylation produced by commonly used cellular host such as CHO cells. In contrast, the present invention provides lower eukaryotic host cells that have been engineered to produce recombinant erythropoietins comprising pre-selected desired N-glycan structures. The compositions of recombinant erythropoietins produced therefrom are significantly greater in uniformity of glycoforms than those produced in CHO cells.

Erythropoietin is a protein hormone which has been widely used for therapeutic indications requiring increased formation of red blood cells including anemia due to renal failure or chemotherapy treatment. Because of the great demand for safe and effective erythropoietin, recombinant human erythropoietin has become the largest selling recombinant human protein product.

Native human erythropoietin contains four carbohydrate chains (three N-linked and one O-linked). The protein requires tri- and tetra-antennary sialylated N-glycans for maximum in vivo efficacy. However, in vitro receptor binding and cell-based assays reveal that erythropoietins with multi-branched sialylated glycans and erythropoietins with additional N-glycosylation sites exhibit decreased binding relative to enzymatically deglycosylated erythropoietin. This paradox can be explained by considering clearance from the circulatory system. Tetra-antennary sialylated erythropoietin and darbepoetin exhibit longer serum half-lives compared with bi-antennary sialylated and nonglycosylated erythropoietin. (The principal routes of clearance for erythropoietin are via renal filtration, through binding to the asialoglycoprotein receptor, endothelial cell uptake and internalization by the target cell through the erythropoietin receptor.)

Currently marketed forms of recombinant erythropoietin include Epogen with three tetra-antennary N-glycan structures and Aranesp, erythropoietin engineered to contain two additional N-glycosylation sites for a total of five tetra-antennary N-glycan structures. The addition of these extra N-glycan attachment sites has resulted in a longer serum half-life and consequently an increased in vivo activity of the hormone. These erythropoietins are produced from CHO cells and secreted with a heterogeneous mixture of N-glycan structures. Process development is used to enrich for the tetra-antennary sialylated glycoform (see FIG. 1).

Past efforts to improve upon the properties of erythropoietin have included efforts to alter the glycosylation, for example by adding glycosylation sites, as well as efforts to conjugate the protein to polymers, such as polyethylene glycols. See, for example EP 0640619; WO 00/32772 WO 01/02017 and WO 03/029291. Despite these attempts, there remains a need for recombinant erythropoietin having improved properties such as greater ease of administration; less rigorous dosage regimens; improved pharmacokinetics and bioavailability; and less expensive manufacture. In particular, robust processes and materials useful to produce compositions of erythropoietin possessing these qualities from lower eukaryotic cells has remained an elusive and desirable goal.

SUMMARY OF THE INVENTION

Accordingly, the present invention provides methods and materials for production of vectors and host cells which are capable of expressing recombinant human erythropoietin with specifically directed N-glycosylation, as well as compositions of recombinantly engineered glycoproteins which have been chemically modified, for example, by PEGylation.

The present invention provides engineered strains of lower eukaryotes, particularly, *Pichia pastoris*, which are capable of producing fully sialylated recombinant EPO with bi-antennary N-glycan structures.

The present invention also provides a PEGylated EPO with bi-antennary glycans. These recombinant glycoprotein compositions exhibit the enhanced in vivo bio-activity previously seen in vitro while maintaining increased serum half-life Thus, the present invention provides methods and materials for the production of compositions of PEGylated erythropoietin protein, said composition comprising a plurality of N-linked glycoforms comprising at least one N-linked glycan attached thereto. In preferred embodiments the composition comprises a plurality of N-linked glycans in which greater than 25 mole percent of said plurality of N-linked glycans consists essentially of a desired N-linked glycan structure selected from the group consisting of:
$GlcNAc_2Man_3GlcNAc_2Gal_2NANA_2$;
$GlcNAc_2Man_3GlcNAc_2Gal_2$; $GlcNAc_2Man_3GlcNAc_2$;
$GlcNAc_2Man_3$; $GlcNAc_2Man_5GlcNAcGalNANA$;
$GlcNAc_2Man_5GlcNAcGal$;
$GlcNAc_2Man_5GlcNAc$; and $GlcNAc_2Man_5$.

In further preferred embodiments, the desired N-linked glycans structure comprises greater than 50 mole percent; 75 mole percent or 80 mole percent of said N-linked glycan structures.

In one preferred embodiment, the desired N-linked glycan structure consists essentially of $GlcNAc_2Man_3GlcNAc_2Gal_2NANA_2$.

In further preferred embodiments, the PEGylated erythropoietin protein composition comprising a plurality of glycoforms, each glycoform comprising at least one N-linked glycan attached thereto, wherein the glycoprotein composition thereby comprises a plurality of N-linked glycans in which greater than 25 mole percent of said plurality of N-linked linked glycans consists essentially of $GlcNAc_2Man_3GlcNAc_2Gal_2NANA_2$.

In further preferred embodiments, the present invention comprises compositions in which greater than 50 mole percent; 75 mole percent or 80 mole percent of said plurality of N-linked glycans consists essentially of $GlcNAc_2Man_3GlcNAc_2Gal_2NANA_2$.

In further preferred embodiments, the present invention comprises compositions of PEGylated erythropoietin in which the $GlcNAc_2Man_3GlcNAc_2Gal_2NANA_2$ N-linked glycan is present at a level from about 5 mole percent to about 80 mole percent more than the next most predominant N-linked glycan structure of said plurality of N-linked glycans.

Another preferred glycoform of the present invention consists essentially of the structure $GlcNAc_2Man_3GlcNAc_2Gal_2$. In preferred embodiments, the PEGylated erythropoietin protein composition comprising a plurality of glycoforms, each glycoform comprising at least one N-linked glycan attached thereto, wherein the glycoprotein composition thereby comprises a plurality of N-linked glycans in which greater than 25 mole percent of said plurality of N-linked linked glycans consists essentially of $GlcNAc_2Man_3GlcNAc_2Gal_2$.

In further preferred embodiments, the present invention comprises compositions in which greater than 50 mole percent greater than 75 mole percent of said plurality of N-linked glycans consists essentially of $GlcNAc_2Man_3GlcNAc_2Gal_2$.

In further preferred embodiments, the present invention comprises compositions of PEGylated erythropoietin in which the $GlcNAc_2Man_3GlcNAc_2Gal_2$ N-linked glycan is present at a level from about 5 mole percent to about 80 mole percent more than the next most predominant N-linked glycan structure of said plurality of N-linked glycans.

In preferred compositions of the present invention, a polyethylene glycol moiety and the N-terminal amino acid residue of erythropoietin protein may be linked, either directly or via a linker.

In preferred embodiments of the invention, the polyethylene glycol moiety may have a molecular weight of from about 5 to about 100 kD; more preferably about 20 kD to about 60 kD; weight of from about 30 kD to about 40 kD.

The present invention also provides therapeutic methods employing the recombinant erythropoietins. In preferred embodiments the recombinant erythropoietin is administered to a human patient in need of treatment to alleviate an anemia. In further preferred embodiments, the patient is treated for anemia induced by renal failure, chemotherapy or cancer.

BRIEF DESCRIPTION OF THE DRAWINGS

FIG. 1A-1D illustrates the stepwise creation of the *P. pastoris* strain YGLY3159 that secretes human recombinant EPO on which the predominant N-glycan is a fully sialylated glycan, represented as: $GlcNAc_2Man_3GlcNAc_2Gal_2NANA_2$.

BRIEF DESCRIPTION OF THE SEQUENCES

Figure 1A:
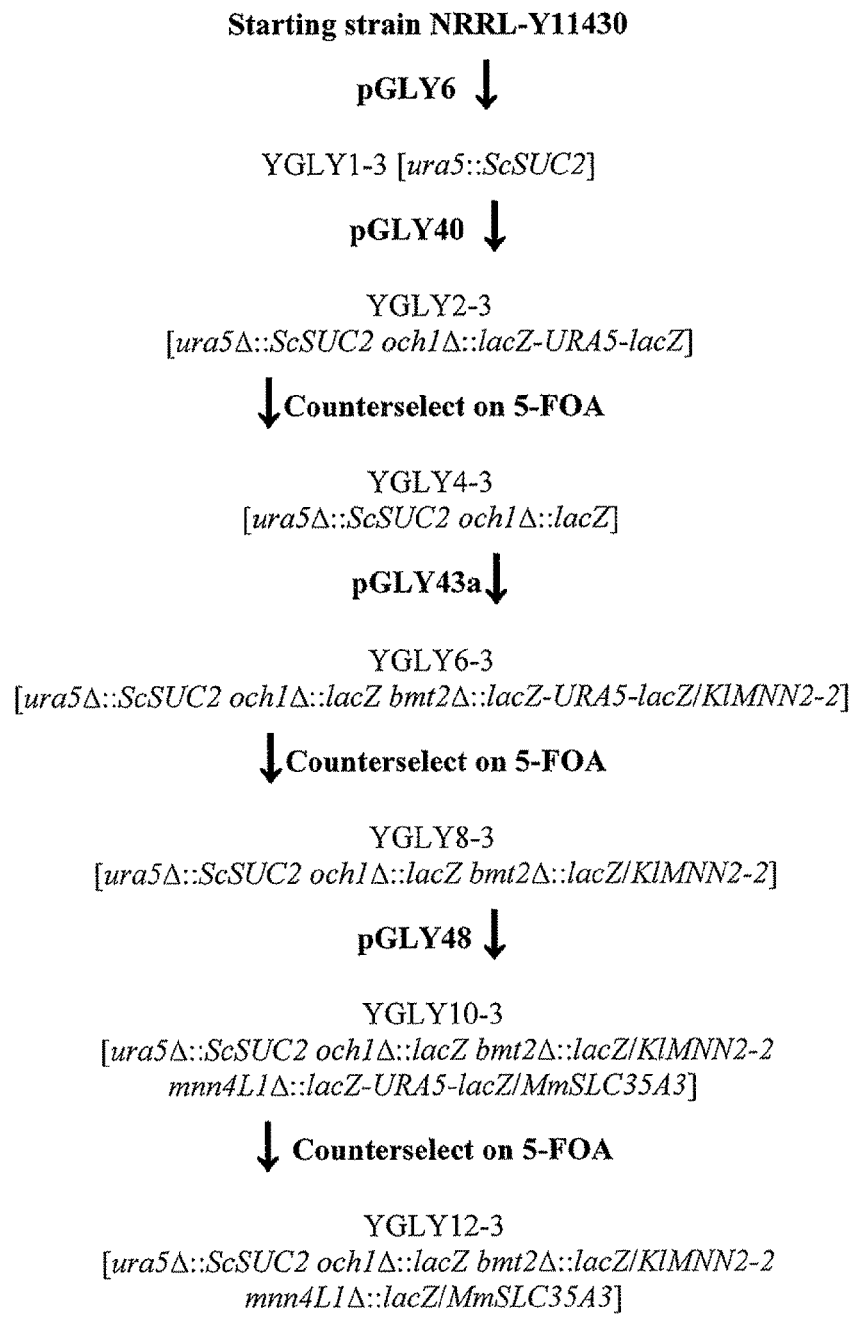

SEQUENCE ID NO: 1 A DNA sequence encoding a human erythropoietin.
SEQUENCE ID NO: 2 Amino acid sequence encoding a human erythropoietin.

DETAILED DESCRIPTION OF THE INVENTION

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of Biochemistry: Section A Proteins*, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

Abbreviations used herein are of common usage in the art, see, e.g., abbreviations of sugars, above. Other common abbreviations include "PNGase", or "glycanase" or "glucosidase" which all refer to peptide N-glycosidase F (EC 3.2.2.18).

An "isolated", "purified" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated", purified or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" in reference nucleic acid sequence encompasses nucleic acid sequences that can be translated, according to the genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.*

215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and most preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$, for the specific DNA hybrid under a particular set of conditions. The $T_m$ is the temperature at which 50% of the target sequence hybridizes to a perfectly matched probe. See Sambrook et al., *Molecular Cloning: A Laboratory Manual*, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique*, 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "vector" as used herein is intended to refer to a nucleic acid molecule capable of transporting another nucleic acid to which it has been linked into a host cell. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

As used herein, the term "sequence of interest" or "gene of interest" refers to a nucleic acid sequence, typically encoding a protein of interest or a polypeptide of interest, that is not normally expressed in the host cell. A sequence or gene of interest includes genes and sequences that are heterologous to the host cell. Proteins and polypeptides of interest are also often heterologous to the host cell. The methods disclosed herein allow one or more sequences of interest or genes of interest to be stably integrated into a host cell genome. Non-limiting examples of sequences of interest include sequences encoding one or more polypeptides of interest having an enzymatic activity, e.g., an enzyme which affects N-glycan synthesis in a host such as mannosyltransferases, N-acetylglucosaminyltransferases, UDP-N-acetylglucosamine transporters, galactosyltransferases, UDP-N-acetylgalactosyltransferase, sialyltransferases and fucosyltransferases.

The term "marker sequence" or "marker gene" refers to a nucleic acid sequence capable of expressing an activity that allows either positive or negative selection for the presence or absence of the sequence within a host cell. For example, the *P. pastoris* URA5 gene is a marker gene because its presence can be selected for by the ability of cells containing the gene to grow in the absence of uracil. Its presence can also be selected against by the inability of cells containing the gene to grow in the presence of 5-FOA. Marker sequences or genes do not necessarily need to display both positive and negative selectability. Non-limiting examples of marker sequences or genes from *P. pastoris* include ADE1, ARG4, HIS4 and URA3. For antibiotic resistance marker genes, kanamycin, neomycin, geneticin (or G418), paromomycin and hygromycin resistance genes are commonly used to allow for growth in the presence of these antibiotics.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which influence the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Preferred host cells are yeasts and fungi.

The term "eukaryotic" refers to a nucleated cell or organism, and includes insect cells, plant cells, mammalian cells, animal cells and lower eukaryotic cells.

The term "lower eukaryotic cells" includes yeast, fungi, collar-flagellates, microsporidia, alveolates (e.g., dinoflagellates), stramenopiles (e.g, brown algae, protozoa), rhodophyta (e.g., red algae), plants (e.g., green algae, plant cells, moss) and other protists.

The terms "yeast" and "fungi" include, but are not limited to: *Pichia* sp., *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Saccharomyces* sp., *Saccharomyces cerevisiae, Hansenula polymorpha, Kluyveromyces* sp., *Kluyveromyces lactis, Candida albicans, Aspergillus* sp., *Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*.

The term "peptide" as used herein refers to a short polypeptide, e.g., one that is typically less than about 50 amino acids long and more typically less than about 30 amino acids long. On of skill in the art can make derivatives, mutants, analogs and mimetics that mimic structural and thus biological function.

The term "polypeptide" encompasses both naturally-occurring and non-naturally-occurring proteins and fragments thereof. A polypeptide may be monomeric or polymeric. Further, a polypeptide may comprise a number of different domains each of which has one or more distinct activities. One of skill in the art can make or isolate mutants, derivatives and analogs of polypeptides.

The terms "purified" or "isolated" protein or polypeptide refers to a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free or purified of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and anti-ligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference). The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide, preferably at least 20 or 30 amino acids, more preferably at least 40, 50 or 60 amino acids, and often more preferably at least 75, 100 or 125 amino acids. Fusions that include the entirety of the proteins of interest have particular utility. The heterologous polypeptide included within the fusion protein is at least 6 amino acids in length, often at least 8 amino acids in length, and usefully at least 15, 20, and 25 amino acids in length. Fusions also include larger polypeptides, or even entire proteins, such as the green fluorescent protein ("GFP")

chromophore-containing proteins having particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic". See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W, H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) In a preferred embodiment, a homologous protein is one that exhibits at least 65% sequence homology to the wild type protein, more preferred is at least 70% sequence homology. Even more preferred are homologous proteins that exhibit at least 75%, 80%, 85% or 90% sequence homology to the wild type protein. In the most preferred embodiment, a homologous protein exhibits at least 95%, 98%, 99% or 99.9% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using PASTA, a program in GCG Version 6.1. PASTA provides alignments and percent sequence identity of the regions of the best overlap between the query and search sequences. Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule.

As used herein, the term "molecule" means any compound, including, but not limited to, a small molecule, peptide, protein, sugar, nucleotide, nucleic acid, lipid, etc., and such a compound can be natural or synthetic.

As used herein, the term "comprise" or variations such as "comprises" or "comprising", will be understood to imply the inclusion of a stated integer or group of integers but not the exclusion of any other integer or group of integers.

When referring to "mole percent" of a glycan present in a preparation of a glycoprotein, the term means the molar percent of a particular glycan present in the pool of N-linked oligosaccharides released when the protein preparation is treated with PNG'ase and then quantified by a method that is not affected by glycoform composition, (for instance, labeling a PNG'ase released glycan pool with a fluorescent tag such as 2-aminobenzamide and then separating by high performance liquid chromatography or capillary electrophoresis and then quantifying glycans by fluorescence intensity). For example, 50 mole percent $GlcNAc_2Man_3GlcNAc_2Gal_2NANA_2$ means that 50 percent of the released glycans are $GlcNAc_2Man_3GlcNAc_2Gal_2NANA_2$ and the remaining 50 percent are comprised of other N-linked oligosaccharides. In embodiments, the mole percent of a particular glycan in a preparation of glycoprotein will be between 20% and 100%, preferably above 25%, 30%, 35%, 40% or 45%, more preferably above 50%, 55%, 60%, 65% or 70% and most preferably above 75%, 80% 85%, 90% or 95%.

As used herein, the term "predominantly" or variations such as "the predominant" or "which is predominant" will be understood to mean the glycan species that has the highest mole percent (%) of total N-glycans after the glycoprotein has been treated with PNGase and released glycans analyzed by mass spectroscopy, for example, MALDI-TOF MS. In other words, the phrase "predominantly" is defined as an individual entity, such as a specific glycoform, is present in greater mole percent than any other individual entity. For example, if a composition consists of species A in 40 mole percent, species B in 35 mole percent and species C in 25 mole percent, the composition comprises predominantly species A.

The term "therapeutically effective amount" refers to an amount of the recombinant erythropoietin of the invention which gives an increase in hematocrit that provides benefit to a patient. The amount will vary from one individual to another and will depend upon a number of factors, including the overall physical condition of the patient and the underlying cause of anemia. For example, a therapeutically effective amount of erythropoietin of the present invention for a patient suffering from chronic renal failure can be in the range of 20 to 300 units/kg or 0.5 ug/kg to 500 ug/kg based on therapeutic indication. The term "unit" refers to units commonly known in the art for assessing the activity of erythropoietin compositions. A milligram of pure erythropoietin is approximately equivalent to 150,000 units. A dosing schedule can be from about three times per week to about once every four or six weeks. The actual schedule will depend on a number of factors including the type of erythropoietin administered to a patient (EPO or PEGylated-EPO) and the response of the individual patient. The higher dose ranges are not typically used in anemia applications but can be useful on other therapeutic applications. The means of achieving and establishing an appropriate dose of erythropoietin for a patient is well known and commonly practiced in the art.

Variations in the amount given and dosing schedule from patient to patient are including by reference to the term "about" in conjunction with an amount or schedule. The amount of erythropoietin used for therapy gives an acceptable rate of hematocrit increase and maintains the hematocrit at a beneficial level (for example, usually at least about 30% and typically in a range of 30% to 36%). A therapeutically effective amount of the present compositions may be readily ascertained by one skilled in the art using publicly available materials and procedures. Additionally, iron may be given to the patient to maintain increased erythropoiesis during therapy. The amount to be given may be readily determined by methods commonly used by those skilled in the art.

The erythropoietin of the present invention may thus be used to stimulate red blood cell production and correct depressed red cell levels. The most common therapeutic application of erythropoietin is to correct red cell levels that are decreased due to anemia. Among the conditions treatable by the present invention include anemia associated with a decline or loss of kidney function (chronic renal failure), anemia associated with myelosuppressive therapy, such as chemotherapeutic or anti-viral drugs (such as AZT), anemia associated with the progression of non-myeloid cancers, and anemia associated with viral infections (such as HIV). Additionally, erythropoietin of the present invention can be used to prevent or lessen neuronal damage following stroke (particularly a non-sialylated epo), congestive heart failure, in the treatment of spinal injury; i.e., anti-inflammatory, anti-apoptosis and the recruitment of stem cells apart from erythropoiesis. Also treatable are conditions which may lead to anemia in an otherwise healthy individual, such as an anticipated loss of blood during surgery. In general, any condition treatable with erythropoietins generally can be treated with the erythropoietins of the present invention.

I. Glycosylation

Figure 9A:
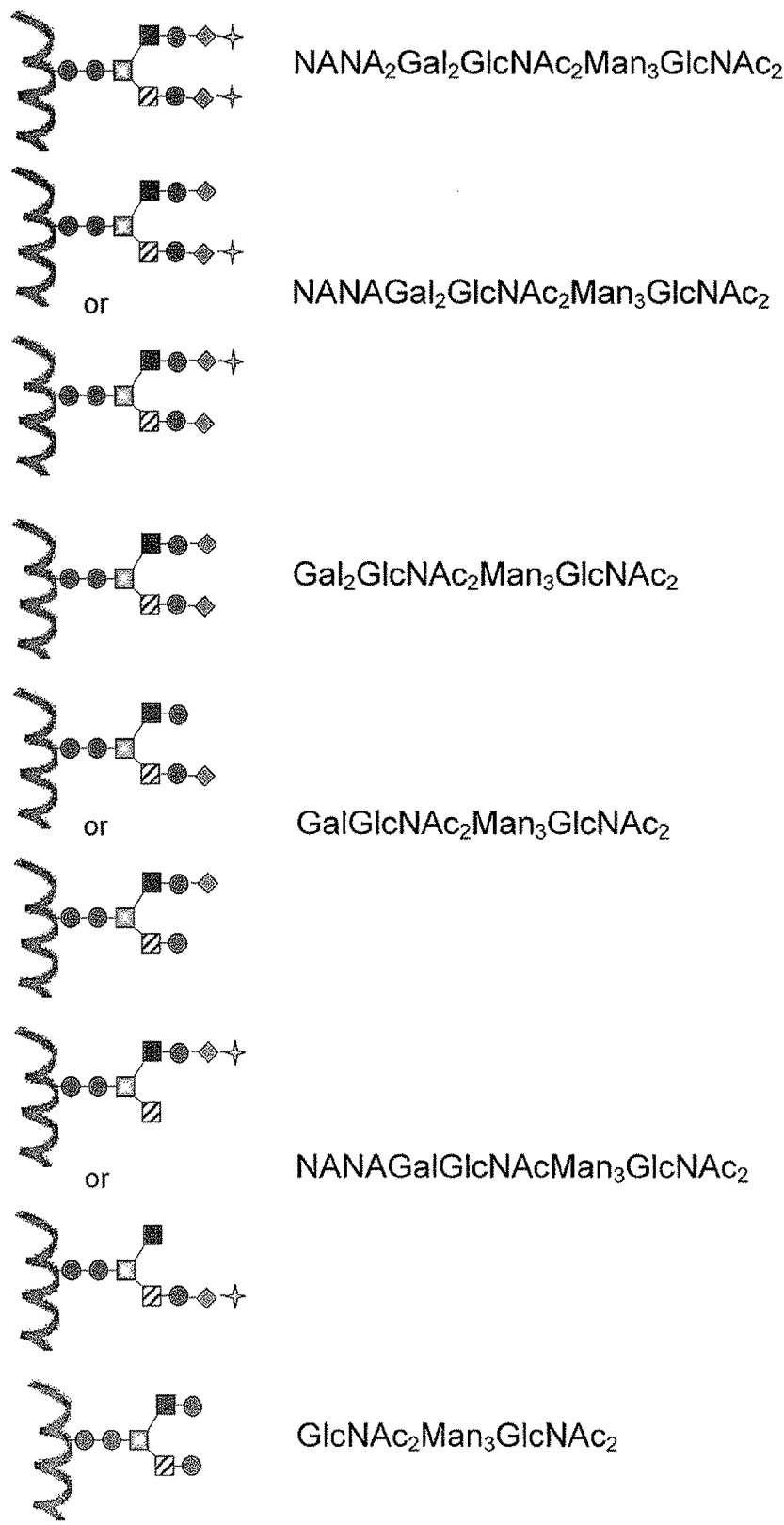
FIGS. 9A-9B show preferred N-linked glycoforms of erythropoietin which may be produced in accordance with the present invention.
Figure 9B:
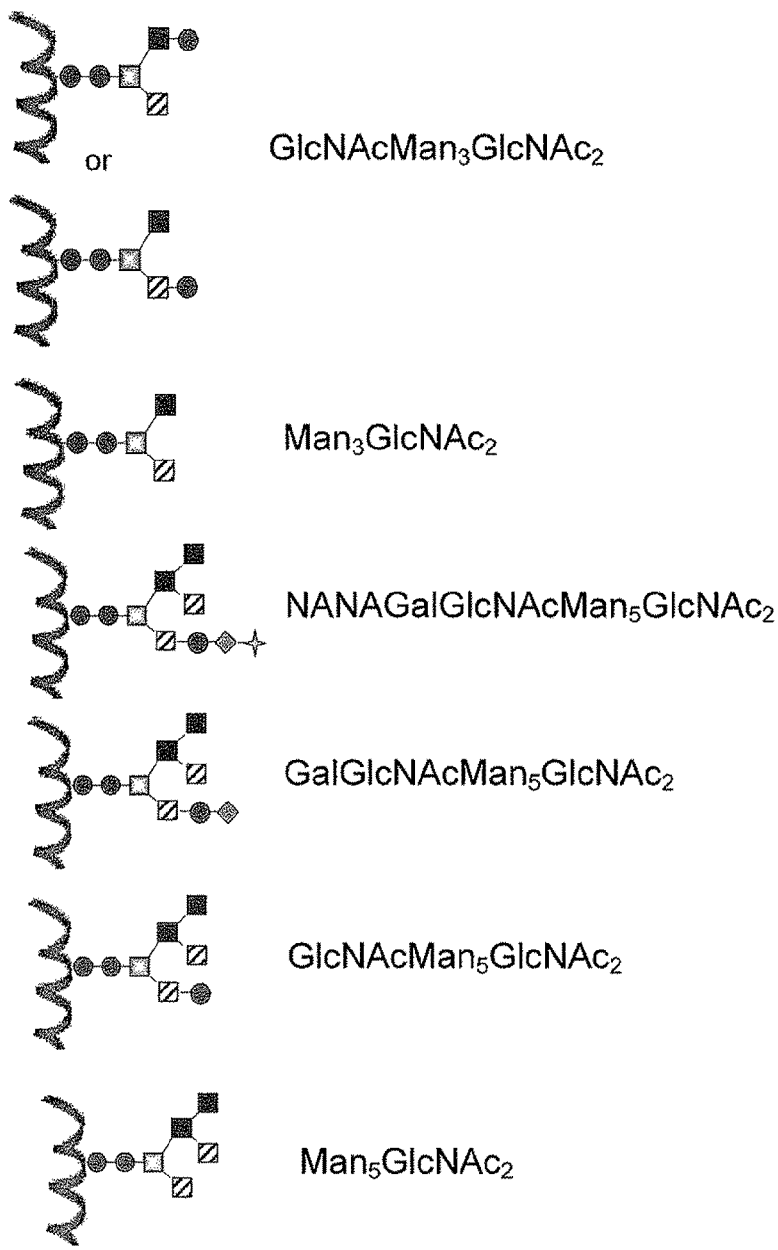

The invention provides methods and materials for the transformation, expression and selection of recombinant proteins, particularly erythropoietin, in lower eukaryotic host cells, which have been genetically engineered to produce glycoproteins with specific desired N-glycans as the predominant species. In certain embodiments, the eukaryotic host cells have been genetically engineered to produce erythropoietin, or a variant of erythropoietin, with a specific desired N-glycan as the predominant species. In preferred embodiments, the predominant N-glycan is one which is not immunogenic to mammals, particularly humans, or which has reduced immunogenicity compared to that of hypermannosylated glycoproteins. Exemplary glycosylation patterns are shown in FIGS. 9A-9B.

In a specific preferred embodiment, the predominant N-glycan is a fully sialylated glycan, represented as: $GlcNAc_2Man_3GlcNAc_2Gal_2NANA_2$. In other preferred embodiments, the predominant N-glycan may be partially sialylated or asialylated glycan; fully galactosylated; partially galactosylated; or agalactosylated. Thus, preferred embodiments include those in which the predominant N-glycan is $GlcNAc_2Man_3GlcNAc_2Gal_2NANA$; $GlcNAc_2Man_3GlcNAc_2GalNANA$; $GlcNAc_2Man_3GlcNAc_2Gal_2$; $GlcNAc_2Man_3GlcNAc_2Gal$, $GlcNAc_2Man_3GlcNAcGal$; $GlcNAc_2Man_3GlcNAc_2$, $GlcNAc_2Man_3GlcNAcr$ or $GlcNAc_2Man_3$. In other preferred embodiments, the predominant N-glycan is a partially galactosylated glycans, represented as $GlcNAc_2Man_3GlcNAc_2Gal_n$, where n may be 1 or 2.

In other embodiments of the present invention, the predominant N-glycan may be a hybrid glycoform, represented by the formula: $GlcNAc_2Man_{(4-5)}GlcNAc_{(0-1)}Gal_{(0-1)}NANA_{(0-1)}$. Preferred embodiments include those in which the predominant N-glycan is $GlcNAc_2Man_5GlcNAcGal$ NANA, $GlcNAc_2Man_5GlcNAcGal$; and $GlcNAc_2Man_5GlcNAc$ and $GlcNAc_2Man_5$.

Many wild-type lower eukaryotic cells, including yeasts and fungi, such as *Pichia pastoris*, produce glycoproteins without any core fucose. Thus, in the above embodiments, the recombinant glycoproteins produced in accordance with the present invention may lack fucose, or be essentially free of fucose. Alternatively, in certain embodiments, the recombinant lower eukaryotic host cells may be genetically modified to include a fucosylation pathway, thus resulting in the production of recombinant glycoprotein compositions in which the predominant N-glycan species is fucosylated. Unless specifically noted, the glycoprotein compositions of the present invention may be produced either in afucosylated form, or with core fucosylation present.

In the present invention, the recombinant glycoprotein produced in accordance with the above description is then chemically modified to improve its physical characteristics, notably serum half-life and pharmacokinetics. In preferred embodiments, the chemical modification is accomplished by linking one or more polyethylene glycol (PEG) moieties to said recombinant glycoprotein, resulting in a PEGylated glycoprotein. In certain preferred embodiments, the recombinant glycoprotein is modified by linking one or more PEG moieties to the N-terminal amino acid of the recombinant glycoprotein, resulting in an N-terminally PEGylated glycoprotein.

II Erythropoietin

Erythropoietin (EPO) is a haemopoietic glycoprotein produced in the kidney that stimulates the differentiation of late erythroid progenitor cells to mature red blood cells. Erythropoietin exerts its biological activity by binding to receptors on erythroid precursors. The erythropoietin gene is not particular to humans. Analogous genes have been found in other species, including many mammals (See Wen et al., Blood (1993); 82:1507-16). Therefore, both human and non-human genes can be expressed as described herein and the variety of erythropoietins may also be useful in the methods of the present invention.

Naturally occurring human erythropoietin is first translated to a 166 amino acid containing polypeptide chain with arginine at position 166. In a postranslational modification, arginine 166 is cleaved by a carboxypeptidase. The primary structure of 165 amino acid human erythropoietin is shown in SEQ ID NO:2 and a nucleic acid this EPO is shown in SEQ ID NO:1. The secondary structure of erythropoietin includes two disulfide bridges between Cys7-Cys161 and Cys29-Cys33. Fully glycosylated EPO comprises approximately 40% carbohydrate groups by molecular weight (Sasaki, H., et al., J. Biol. Chem. 262 (1987) 12059-12076). The molecular weight of the polypeptide chain of human erythropoietin without the glycan moieties is 18,236 Da.

Because erythropoietin is essential in red blood cell formation, it is useful in the treatment of blood disorders characterized by low or defective red blood cell production. Clinically, erythropoietin is used in the treatment of various ailments, for example, anemia in chronic renal failure patients (CRF) and in AIDS and cancer patients undergoing chemotherapy (Danna, R. P., et al., In: M B, Garnick, ed. Erythropoietin in Clinical Applications—An International Perspective. New York, N.Y.: Marcel Dekker; 1990, pp. 301-324). However, the bioavailability of currently available protein therapeutics such as erythropoietin is limited by their short plasma half-life and susceptibility to protease degradation. These shortcomings prevent them from attaining maximum clinical potency. Modifications of the amino acid sequence of EPO have been disclosed, for example, in a number of references including U.S. Pat. No. 4,835,260; WO 94/25055; WO 94/24160; WO 94/02611; WO 95/05465.

Erythropoietin has been manufactured biosynthetically using recombinant DNA technology (Egrie, J. C., et al., Immunobiol. 72 (1986) 213-224). Erythropoietin currently used in human therapy is the product of a cloned human EPO gene inserted into and expressed in the ovarian tissue cells of the Chinese hamster (CHO cells). Both human urinary derived erythropoietin and recombinant erythropoietin (expressed in mammalian cells) contain three N-linked and one O-linked oligosaccharide chains which together comprise about 40% of the total molecular weight of the glycoprotein. N-linked glycosylation occurs at asparagine residues located at positions 24, 38 and 83 while O-linked glycosylation occurs at a serine residue located at position 126 (Lai, et al., J. Biol. Chem. 261 (1986) 3116; Broudy, V. C., et al., Arch. Biochem. Biophys. 265 (1988) 329). The oligosaccharide chains have been shown to be modified with terminal sialic acid residues. Enzymatic treatment of glycosylated erythropoietin to remove all sialic acid residues results in a loss of in vivo activity but does not affect in vitro activity (Lowy et al., Nature 185 (1960) 102; Goldwasser, E., et al. J. Biol. Chem. 249 (1974) 4202-4206). This behavior has been explained by rapid clearance of asialoerythropoietin from circulation upon interaction with the hepatic asialoglycoprotein binding protein (Morrell et al., J. Biol. Chem. 243 (1968) 155; Briggs, D. W., et al., Am. J. Physiol. 227 (1974) 1385-1388; Ashwell, G., and Kawasaki, T., Methods Enzymol. 50 (1978) 287-288). Thus, erythropoietin possesses in vivo biological activity only when it is sialylated to avoid its binding by the asialoglycoprotein binding protein.

The role of the other components in the oligosaccharide chains of erythropoietin has not been well defined. It has been shown that partially diglycosylated erythropoietin has greatly reduced in vivo activity compared to the glycosylated form but does retain in vitro activity. (Dordal, M. S., et al., Endocrinology 116 (1985) 2293-2299). In another study, however, the removal of N-linked or O-linked oligosaccharide chains singly or together by mutagenesis of asparagine or serine residues that are glycosylation sites sharply reduces biological activity of the altered erythropoietin that is produced in mammalian cells (Dube, S., et al., J. Biol. Chem. 263 (1988) 1751647521).

Oligonucleotide-directed mutagenesis has been used to prepare structural mutants of EPO lacking specific sites for glycosylation (Yamaguchi, K., et al., J. Biol. Chem. 266 (1991) 20434-20439; and Higuchi, M., et al., J. Biol. Chem. 267 (1992) 7703-7709). Cloning and expression of non-glycosylated EPO in *E. coli* is described by Lee-Huang, S., Proc. Natl. Acad. Sci. USA 61 (1984) 2708-2712; and in U.S. Pat. No. 5,641,663.

EP 0 640 619 relates to analogs of human erythropoietin comprising an amino acid sequence which includes at least one additional site for glycosylation. The added sites for glycosylation may result in a greater number of carbohydrate chains, and higher sialic acid content, than human erythropoietin. Erythropoietin analogs comprising amino acid sequences which include the rearrangement of at least one site for glycosylation are also provided. Analogs comprising an addition of one or more amino acids to the carboxy terminal end of erythropoietin wherein the addition provides at least one glycosylation site are also included.

Compared to erythropoietin produced in CHO cells, erythropoietin produced in *Pichia* with humanized glycosylation is much more uniform in the attached oligosaccharide structures that comprise N- and O-glycosylation. CHO-derived rhEPO is produced with a mixture of glycoforms, including bi-, tri- and tetra-antennary forms with varying amounts of sialylation. Process development is used to enrich for tetra-antennary sialylated glycoforms which comprise a small portion of the of N-glycans pre-enrichment (Restelli et al, 2006 Biotechnology and Bioengineering 94 (3) p. 481-494). Additionally, while sialylation in humanized yeast does not include N-glycolylneuraminic acid (NGNA), sialyated erythropoietin produced in CHO cells contains a mixture of NANA (N-acetylneuraminic acid) and NGNA.

Erythropoietins produced in mammalian cell lines, such as Chinese hamster ovary (CHO) cells are enriched for carbohydrates that contain sialylated N-linked glycans. Enriching for tetra-antennary glycoforms increases the proportion of lactosamine repeats on N-glycans of erythropoietin. Erythropoietin molecules containing these repeats may possess impaired in vivo efficacy as presence of polylactosamine repeats has been correlated with rapid clearance from the circulation via the liver (Fukuta et al., (1989) *Blood*, Vol. 73, 84).

Lactosamine moieties have also been reported to bind to the galectin family of lectins, carbohydrate binding proteins differentially expressed on the cell surface of different cell and tissues types. Specifically, galectin-3 specifically recognizes lactosamine. Galectin-3 has been found to be overexpressed on the cell surface of many different tumor cell types and has been implicated in cell growth, transformation and metastasis (Deininger et al., (2002) *Anticancer Research*, Vol. 22, 1585).

Thus, glycoproteins that contain lactosamine repeats can potentially be targeted to cells expressing galectin-3 on the cell surface. Moreover, this presents a further potential risk that lactosamine-containing glycoproteins may selectively target tumor cells which may coincidentally bear the cognate receptor for the glycoprotein. In the case of erythropoietins, the fraction of erythropoietin that contains lactosamine may preferentially target tumor cells and, if the erythropoietin receptor is present, an aberrant mitogenic signal may arise driving tumor cell growth with metastatic potential.

Erythropoietins produced in *Pichia pastoris* lack undesired glycoforms such as lactosamine repeats. This would likely alleviate concerns relating to the tumorigenic potential of EPO and other glycoproteins.

Other differences include a complete lack of attached core fucose and polylactosamine in *Pichia*-produced erythropoietin, both present on the CHO cell version, and variations on O-glycan composition, with a heterogeneous mixture of O-GalNAc structures on CHO-produced erythropoietin compared to the O-mannose that may be found on *Pichia*-produced erythropoietin. Sialic acid linkage is primarily $\alpha 2,3$ in CHO-produced erythropoietin, with some $\alpha 2,6$ present, while *Pichia*-produced erythropoietin contains exclusively $\alpha 2,6$ (Hamilton, Science Vol 313, p. 1441-1443), similar to human urinary erythropoietin which contains predominantly $\alpha 2,6$ linked sialic acid.

Erythropoietin (EPO) is a tissue-protective cytokine that has been shown to prevent vascular spasm, apoptosis, and inflammatory responses. Although best known for its activity on hematopoiesis, EPO also affects other tissues, including the nervous system. Animal models have demonstrated that single doses of rhEPO are efficacious for the treatment of acute injury (4-6, 19). For instance, infusion of EPO into the lateral ventricle of gerbils subjected to occlusion of the common carotid arteries prevented ischemia-induced learning disability and rescued hippocampal neurons from degeneration (Bernaudin et al. (1999) J Cereb Blood Flow Metab 19, 643).

Studies in vivo have demonstrated the protective effects of EPO on various forms of neuronal damage (Brines et al. (2000), PNAS, 97, 10526; Celik et al. (2002), PNAS, 99, 2258; Junk et al. (2002), PNAS, 99, 10659). However, many clinical situations will likely require multiple doses of rhEPO, which most likely will lead to potentially harmful increases in hematocrit thus curbing enthusiasm for recombinant human erythropoietin (rhEPO) as a potential neuroprotective therapeutic. This is supported by animal models which clearly show that EPO-dependent increases in hematocrit can cause and amplify brain injury. A potential solution to this paradox could be through the use of EPO with bi-antennary glycosylation which has a minimal effect on hematocrit in animal models (Hamilton et al. (2006) Science 313, 1441). Thus multiple high doses of EPO with biantennary glycosylation for the treatment of inflammation may have little effect on overall hematocrit.

Another interesting glycoform that can be used for the treatment of inflammation is a bi-antennary EPO without terminal sialylation. This may also serve as an effective treatment as an anti-inflammatory agent without significantly increasing hematocrit. The added advantage for this molecule would be its reduced affinity for the asialo-glycoprotein receptor in the liver relative to the preferred substrates of this receptor which are the tri- and tetra-antennary terminally galactosylated glycoforms. Therefore the advantages of an EPO with biantennary asialylated glycosylation are reduced liver clearance, little effect on hematocrit and preferred neuronal tissue distribution. Asialo-EPO can be made according to this invention by expressing EPO in yeast cells lacking the sialyation portion of the glycosylation pathway shown herein.

III. Nucleic Acid Encoding the Glycoprotein

The erythropoietins of the present invention are encoded by nucleic acids. The nucleic acids can be DNA or RNA, typically DNA. The nucleic acid encoding the glycoprotein is operably linked to regulatory sequences that allow expression of the glycoprotein. Such regulatory sequences include a promoter and optionally an enhancer upstream, or 5', to the nucleic acid encoding the fusion protein and a transcription termination site 3' or down stream from the nucleic acid encoding the glycoprotein. The nucleic acid also typically encodes a 5' UTR region having a ribosome binding site and a 3' untranslated region. The nucleic acid is often a component of a vector which transfers to nucleic acid into host cells in which the glycoprotein is expressed. The vector can also contain a marker to allow recognition of transformed cells. However, some host cell types, particularly yeast, can be successfully transformed with a nucleic acid lacking extraneous vector sequences.

Nucleic acids encoding desired erythropoietin of the present invention can be obtained from several sources. cDNA sequences can be amplified from cell lines known to express the glycoprotein using primers to conserved regions (see, e.g., Marks et al., *J. Mol. Biol.* 581-596 (1991)). Nucleic acids can also be synthesized de novo based on sequences in the scientific literature. Nucleic acids can also be synthesized by extension of overlapping oligonucleotides spanning a desired sequence of a larger nucleic acid, e.g., genomic DNA (see, e.g., Caldas et al., Protein Engineering, 13, 353-360 (2000)).

The present invention preferably employs a nucleic acid encoding a mammalian erythropoietin and most preferably employs a nucleic acid encoding a human erythropoietin. Human erythropoietin is well known in the art as a 165 or 166 amino acid protein.

The following nucleotide and amino acid sequences are exemplary preferred sequences that can be employed in present invention.

```
EPO nucleotide sequence
                                          [SEQ ID NO: 1]
ATGAGATTTC CTTCAATTTT TACTGCTGTT TTATTCGCAG

CATCCTCCGC ATTAGCTGCT CCACCAAGAT TGATTTGTGA

CTCCAGAGTT TTGGAGAGAT ACTTGTTGGA GGCTAAAGAG

GCTGAGAACA TCACTACTGG TTGTGCTGAA CACTGTTCCT

TGAACGAGAA CATCACAGTT CCAGACACTA AGGTTAACTT

CTACGCTTGG AAGAGAATGG AAGTTGGACA ACAGGCTGTT

GAAGTTTGGC AAGGATTGGC TTTGTTGTCC GAGGCTGTTT

TGAGAGGTCA AGCTTTGTTG GTTAACTCCT CCCAACCATG

GGAACCATTG CAATTGCACG TTGACAAGGC TGTTTCTGGA

TTGAGATCCT TGACTACTTT GTTGAGAGCT TTGGGTGCTC

AGAAAGAGGC TATTTCTCCA CCAGATGCTG CTTCAGCTGC

TCCATTGAGA ACTATCACTG CTGACACTTT CAGAAAGTTG

TTCAGAGTTT ACTCCAACTT CTTGAGAGGA AAGTTGAAGT

TGTACACTGG TGAAGCTTGT AGAACTGGTG ACTAGTAA

EPO Amino Acid sequence
                                          [SEQ ID NO: 2]
APPRLICDSR VLERYLLEAK EAENITTGCA EHCSLNENIT

VPDTKVNFYA WKRMEVGQQA VEVWQGLALL SEAVLRGQAL

LVNSSQPWEP LQLHVDKAVS GLRSLTTLLR ALGAQKEAIS

PPDAASAAPL RTITADTFRK LFRVYSNFLR GKLKLYTGEA

CRTGD
```

IV. Host Cells

Lower eukaryotic cells, such as yeast and fungi, are preferred for expression of the erythropoietin of the present invention because they can be economically cultured, give high yields, and when appropriately modified are capable of suitable glycosylation. Yeast particularly offers established genetics allowing for rapid transformations, tested protein localization strategies and facile gene knock-out techniques. Suitable vectors have expression control sequences, such as promoters, including 3-phosphoglycerate kinase or other glycolytic enzymes, and an origin of replication, termination sequences and the like as desired.

Various yeasts, such as *K. lactis, Pichia pastoris, Pichia methanolica*, and *Hansenula* polymorphs are preferred for cell culture because they are able to grow to high cell densities and secrete large quantities of recombinant protein. Likewise, filamentous fungi, such as *Trichoderma reesei, Aspergillus niger, Fusarium* sp, *Neurospora crassa* and others can be used to produce glycoproteins of the invention.

Lower eukaryotes, particularly yeast and fungi, can be genetically modified so that they express glycoproteins in which the glycosylation pattern is human-like or humanized. This can be achieved by eliminating selected endogenous glycosylation enzymes and/or supplying exogenous enzymes as described by Gerngross et al., US 20040018590 and U.S. Pat. No. 7,029,872, the disclosures of which are hereby incorporated herein by reference. For example, a host cell can be selected or engineered to be depleted in 1,6-mannosyl transferase activities, which would otherwise add mannose residues onto the N-glycan on a glycoprotein.

Using the methods and materials of the present invention, it is possible to produce glycoprotein compositions comprising a plurality of glycoforms, each glycoform comprising at least one N-glycan attached thereto, wherein the glycoprotein composition thereby comprises a plurality of N-glycans in which a predominant glycoform comprises a desired N-glycan. Utilizing the tools described in Gerngross et al., US 20040018590 and U.S. Pat. No. 7,029,872, together with the present invention, it is possible to produce many different N-linked glycoforms. Depending upon the specific needs, the methods of the present invention can be used to obtain glycoprotein composition in which the predominant N-glycoform is present in an amount between 5 and 80 mole percent greater than the next most predominant N-glycoform; in preferred embodiments, the predominant N-glycoform may be present in an amount between 10 and 40 mole percent; 20 and 50 mole percent; 30 and 60 mole percent; 40 and 70 mole percent; 50 and 80 mole percent greater than the next most predominant N-glycoform. In other preferred embodiments, the predominant N-glycoform is a desired N-glycoform and is present in an amount of greater than 25 mole percent; greater than 35 mole percent; greater than 50 mole percent; greater than 60 mole percent; greater than 75 mole percent; or greater than 80 mole percent of the total number of N-glycans.

In preferred embodiments, a vector can be constructed with one or more selectable marker gene(s), and one or more desired genes encoding erythropoietin which is to be transformed into an appropriate host cell. For example, one or more genes selectable marker gene(s) can be physically linked with one or more gene(s), expressing a desired erythropoietin peptide or protein for isolation or a fragment of said erythropoietin peptide or protein having the desired activity can be associated with the selectable gene(s) within the vector. The selectable marker gene(s) and erythropoietin gene(s) can be arranged on one or more transformation vectors so that presence of the erythropoietin gene(s) in a transformed host cell is correlated with expression of the selectable marker gene(s) in the transformed cells. For example, the two genes can be inserted into the same physical plasmid, under control of a single promoter, or under the control of two separate promoters. It may also be desired to insert the genes into distinct plasmids and co-transformed into the cells.

Other cells useful as host cells in the present invention include prokaryotic cells, such as *E. coli*, and eukaryotic host cells in cell culture, including mammalian cells, such as Chinese Hamster Ovary (CHO).

V. Chemically Modified Erythropoietin

As noted above, polymer vehicles may be conjugated to proteins such as erythropoietin in order to enhance the properties. Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

Chemically modified erythropoietin compositions (i.e., "derivatives"), where the protein or polypeptide is linked to a polymer, are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. Included within the scope of modified erythropoietin compositions is a mixture of polymers. Preferably, for therapeutic use of the end-product preparation, the polymer will be pharmaceutically acceptable.

The water soluble polymer or mixture thereof may be selected from the group consisting of for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol), and poly-vinyl alcohol. For the acylation reactions, the polymer(s) selected should have a single reactive ester group. For reductive alkylation, the polymer(s) selected should have a single reactive aldehyde group. The polymer may be of any molecular weight, and may be branched or unbranched. A particularly preferred water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy or aryloxy-polyethylene glycol.

PEGylation (i.e. modification by the addition of PEG or a PEG derivative), of PAL may be carried out by any of the PEGylation reactions known in the art, as described for example in the following references: Focus on Growth Factors 3:4-10 (1992); EP 0 154 316; and EP 0 401 384. Preferably, the PEGylation is carried out via an acylation reaction or an alkylation reaction with a reactive polyethylene glycol molecule (or an analogous reactive water-soluble polymer), as described below.

In general, chemical derivatization may be performed under any suitable conditions used to react a biologically active substance with an activated polymer molecule. Methods for preparing PEGylated-erythropoietin will generally comprise the steps of (a) reacting an erythropoietin polypeptide with polyethylene glycol (such as a reactive ester or aldehyde derivative of PEG), under conditions whereby erythropoietin becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-PEGylated product.

The present invention also provides a method employing reductive alkylation. for selectively obtaining N-terminally chemically modified erythropoietin. In this method linkage to the N-terminus of erythropoietin can be targeted because of the differential reactivity of different primary amino groups. One chooses a pH wherein the pKa between the $\epsilon$-amino group of lysines in the protein and the $\alpha$-amino group of the N-terminus results in nearly selective derivatization of the protein at the N-terminus by a reaction with a carbonyl group or PEG or another polymer. Mono-polymer modified erythropoietin is preferred. The preparations of this invention will preferably be greater than 50%, 55%, 60%, 65%, 70% or 75% mono-polymer erythropoietin, more preferably greater than 80%, 85% or 90% mono-polymer:protein conjugate, and most preferably greater than 95% mono-polymer-erythropoietin conjugate.

The method of obtaining the mono-polymer derivatized erythropoietin preparation may be by purification of the derivatized material from a population of non-derivatized erythropoietin molecules after the conjugation. For example, presented below is an example where mono-PEGylated erythropoietin is separated using chromatography. Size exclusion chromatography, ion exchange chromatography or a combination of the two and potentially other common purification methods can be used. These methods can be used as analytical tools to characterize the purified products or as a preparative purification tools.

A preferred polymer vehicle is polyethylene glycol (PEG). The PEG group may be of any convenient molecular weight and may be linear or branched. The average molecular weight of the PEG will preferably range from about 2 kiloDalton ("kDa") to about 100 kDa, more preferably from about 5 kDa to about 60 kDa, more preferably from about 20 kDa to about 50 kDa; most preferably from about 30 kDa to about 40 kDa. These PEGs can be supplied from any commericial vendors including NOF Corporation (Tokyo, Japan), Dow Pharma (ChiroTech Technology, Cambridge, UK), Nektar (San Carlos, Calif.) and SunBio (Anyang City, South Korea). Suitable PEG moieties include, for example, 40 kDa methoxy poly (ethylene glycol) propionaldehyde; 60 kDa methoxy poly (ethylene glycol) propionaldehyde; 31 kDa alpha-methyl-w-(3-oxopropoxy), polyoxyethylene; 30 kDa PEG: 30 kDa Methoxy poly(ethylene glycol) propionaldehyde and 45 kDa 2,3-Bis(methylpolyoxyethylene-oxy)-1-[(3-oxopropyl) polyoxyethylene-oxy]-propane. The PEG groups will generally be attached to the compounds of the invention via acylation or reductive amination through a reactive group on the PEG moiety (e.g., an aldehyde, amino, thiol, or ester group) to a reactive group on the protein or polypeptide of interest (e.g., an aldehyde, amino, or ester group). For example, the PEG moiety may be linked to the N-terminal amino acid residue of erythropoietin, either directly or through a linker.

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis (see, for example, FIGS. 5 and 6 and the accompanying text herein). The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for protein modification. Dextrans are polysaccharide polymers comprised of individual subunits of glucose predominantly linked by $\alpha$1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kD to about 20 kD is preferred when dextran is used as a vehicle in accordance with the present invention.

As described above, the presence of a "linker" group is optional. When present, its chemical structure is not critical, since it serves primarily as a spacer. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly $(Gly)_4$, $(Gly)_5$, poly(Gly-Ala), and polyalanines. Other specific examples of linkers are:

$(Gly)_3Lys(Gly)_4$;
$(Gly)_3AsnGlySer(Gly)_2$;
$(Gly)_3Cys(Gly)_4$; and
GlyProAsnGlyGly.

To explain the above nomenclature, for example, $(Gly)_3$ $Lys(Gly)_4$ means Gly-Gly-Gly-Lys-Gly-Gly-Gly-Gly. Combinations of Gly and Ala are also preferred. The linkers shown here are exemplary; linkers within the scope of this invention may be much longer and may include other residues.

Non-peptide linkers are also possible. For example, alkyl linkers such as —NH—$(CH_2)s$-C(O)—, wherein s=2-20 could be used. These alkyl linkers may further be substituted by any non-sterically hindering group such as lower alkyl (e.g., C1-C6) lower acyl, halogen (e.g., Cl, Br), CN, NH2, phenyl, etc. An exemplary non-peptide linker is a PEG linker, wherein n is such that the linker has a molecular weight of 100 to 5000 kD, preferably 100 to 500 kD. The peptide linkers may be altered to form derivatives in the same manner as described above.

PEGylation of glycosylated EPO is described in WO 01/02017. Such molecules show an improved biological activity. WO00/32772 and Francis, G. E., et al., Int. J. Hem. 68 (1988) 1-18, describe polyethylene glycol-modified non-glycosylated EPO. The molecules of WO 00/32772 are additionally modified at positions 166. Such molecules are described as not causing a significant increase in hematocrit. The PEG-polymer portion consists of 1-5 polymer chains. WO 00/32772 suggests to control the degree and site of PEGylation by lowering the pH and reducing the PEG:amine ratio. Reactions run at pH 7 and 1.5:1 molar ratio of PEG-aldehyde: amine groups, preferentially react with the N-terminal α-amino group.

Figure 12:
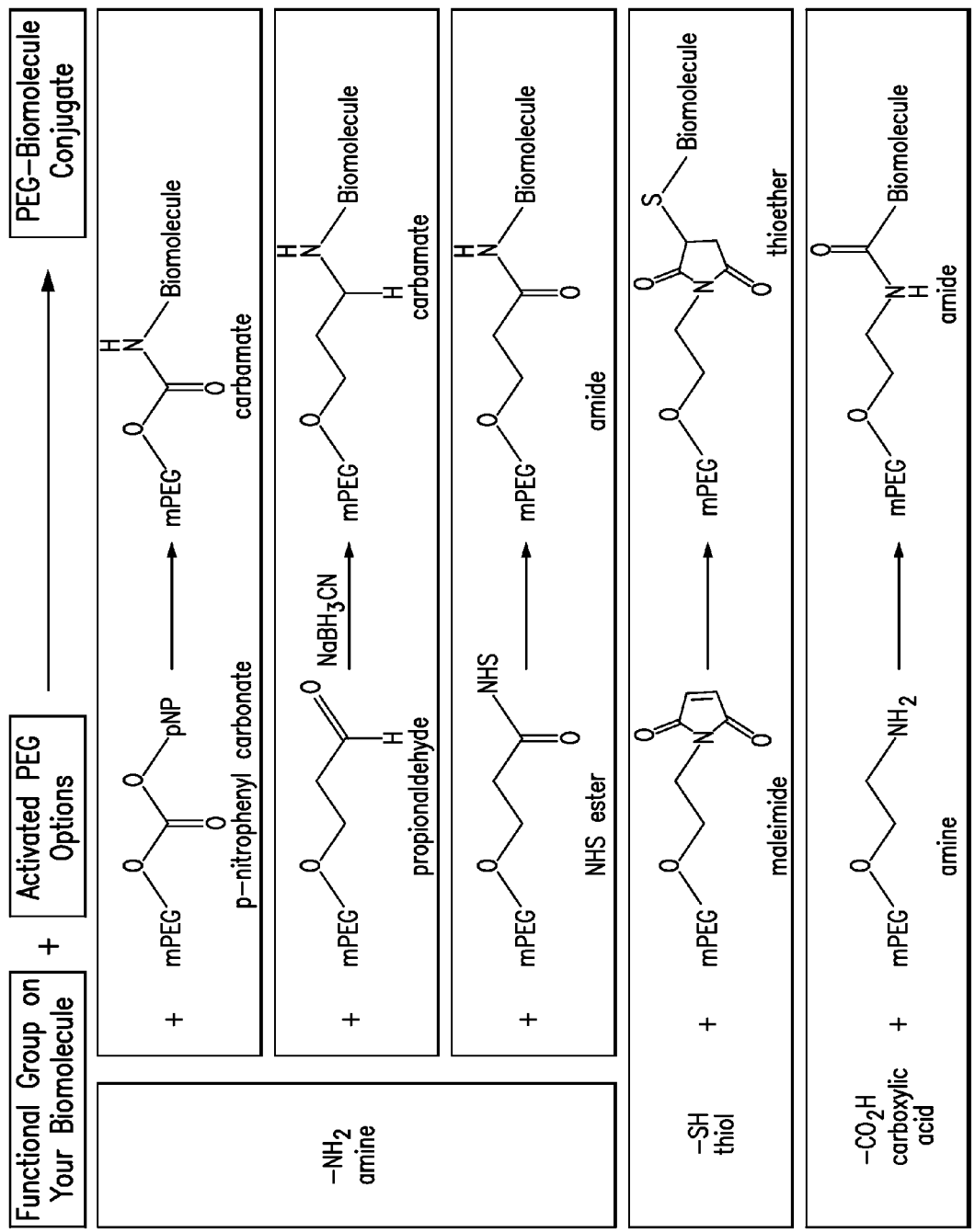
FIG. 12 shows schematic representations of PEGylation chemistries.

Some useful PEGylation linkages are shown in Table 1 and some useful PEGylation reactions are shown in FIG. 12. In a preferred method, N-terminal PEGylation is accomplished through the use of mPEG-propionaldehyde and its covalent conjugation to the rhEPO N-terminus via reductive amination. Selectivity is achieved by exploiting the difference in pKa values between the ε-amino group of lysine (pKa~10) and the N-terminal amino group (pKa~7.6-8.0). In a typical derivatization reaction 30% to 50% of the rhEPO is PEGylated. Higher degrees of derivatization may be achieved under optimized conditions. Mono-PEGylated rhEPO is then purified using a cation exchange chromatography step. Preferably, the purified mono-PEGylated rhEPO is greater than 80%, 85%, 90% or most preferably greater than 95% of the rhEPO after chromatography.

TABLE 1

PEGylation: Reagent selection, PEG-conjugate linkage and conjugate stability

| | Conjugate Linkage Formation |
|---|---|
| Amine PEGylation | |
| mPEG-p-nitrophenyl carbonate | Carbamate |
| mPEG-propionaldehyde and a reducing agent | Secondary amine (stable) |
| mPEG-NHS esters | Amide |
| Thiol PEGylation | |
| mPEG-Maleimide | Thioether |
| Carboxyl PEGylation | |
| mPEG-amine and a coupling agent | Amide (stable) |

Generally, conditions which may be alleviated or modulated by administration of the present polymer/erythropoietin-derivatives include those described herein for erythropoietin molecules in general. However, the polymer/erythropoietin and erythropoietin-derivative molecules disclosed herein may have additional activities, enhanced or reduced activities, or other characteristics, as compared to the non-derivatized molecules

EXAMPLES

Example 1

Construction of the Genetically Engineered *Pichia* 6.0 Cell Line

Following the procedures disclosed in Gerngross U.S. Pat. No. 7,029,872 and Gerngross US 20040018590, one can construct vectors that are useful for genetically engineering lower eukaryotic host cells such that they are capable of expressing a desired polypeptide having a desired N-glycoform as the predominant species. Beginning with the wild-type strain of *Pichia pastoris* NRRL-11430, stepwise introduction of genes is made according to the series described in FIG. 1. The genotype of strain YGLY3159 used herein is ura5Δ::MET16 och1 Δ::lacZ bmt2Δ::lacZ/KlMNN2-2, mnn4L1Δ::lacZ/MmSLC35Δ3 Δpno1Δmnn4Δ::lacZ met16Δ::lacZ, his1Δ::lacZ/ScGAL10/XB33/DmUGT, arg1Δ::HIS1/KD53/TC54, ADE1::lacZ/NA10/ MmSLC35A3/FB8, PRO1::lacZ-URA5-lacZ/TrMDS1, AOX1:Sh ble/AOX1p/ScαMFpre-GFI800, TRP2::ARG1/ MmCST/HsGNE/HsCSS/HsSPS/MmST6-33.

The plasmids used for construction of the strain YGLY3159 are illustrated in FIG. 2, Panels A through O. The plasmids are transformed into the desired cell, in accordance with standard techniques. Suitable techniques for the construction of cell lines are also demonstrated in Hamilton et al., *Science* 313:1441:1443 (2006), the disclosure of which is hereby incorporated herein by reference.

Example 2

Construction of the Vector for Production of Recombinant EPO

Figure 1B:
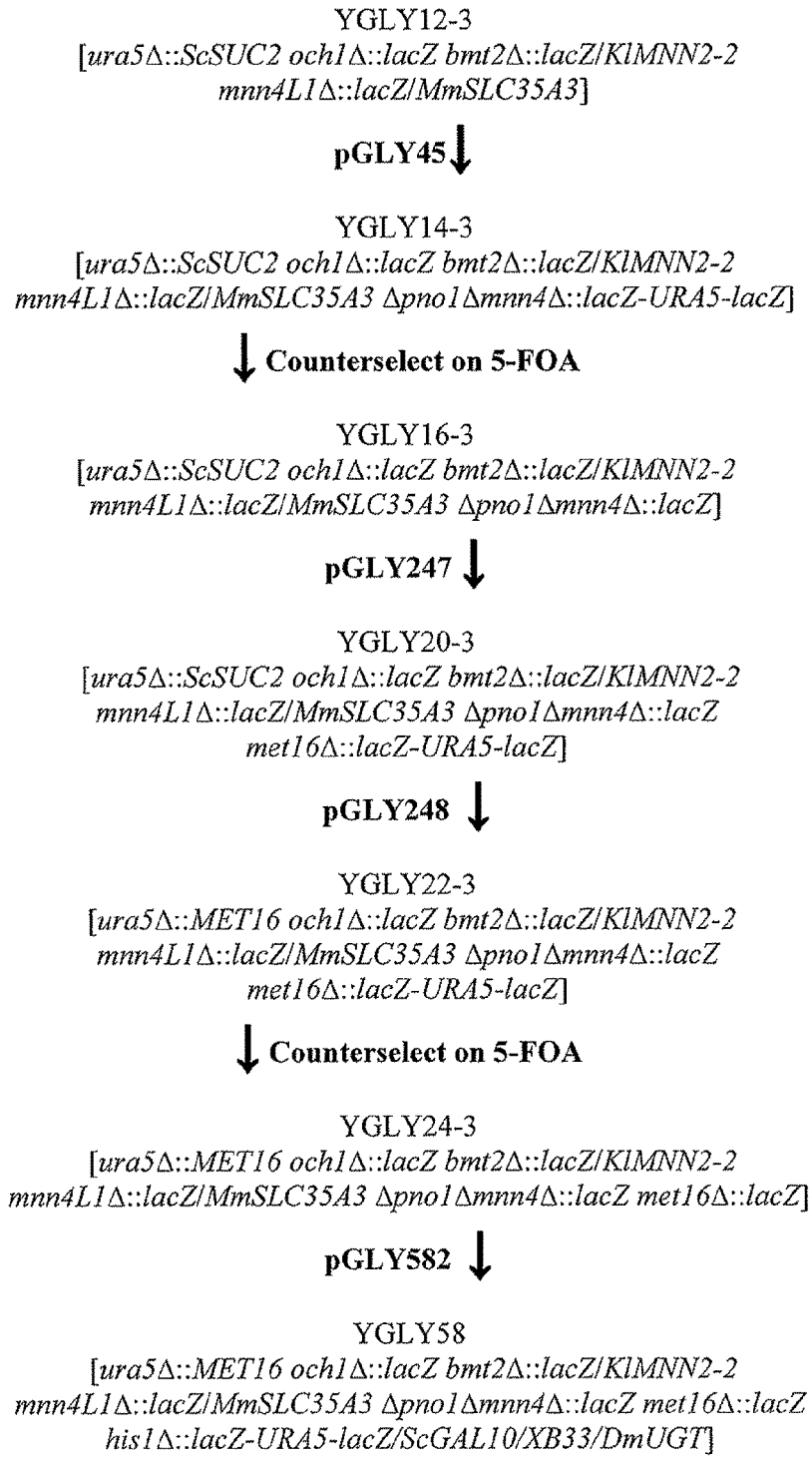
Figure 1C:
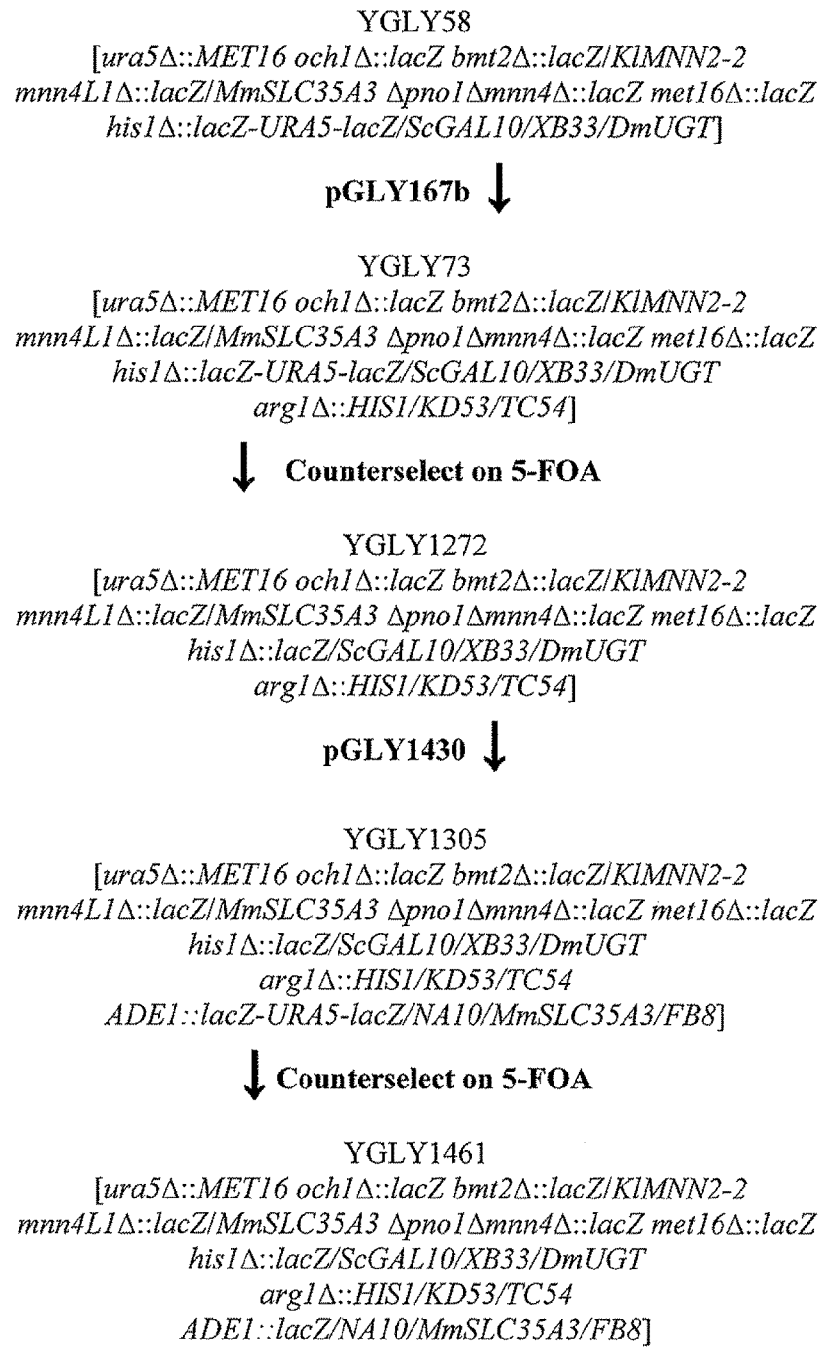
Figure 2A:
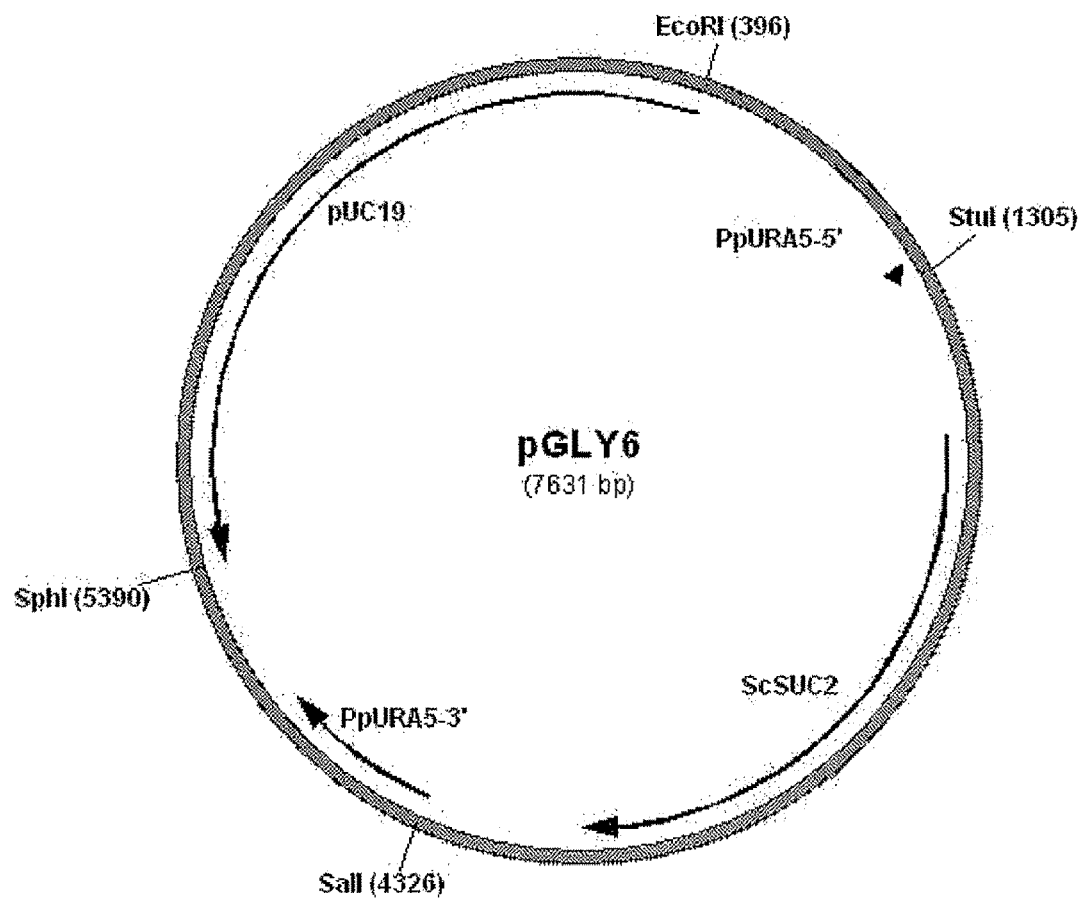
FIG. 2 Panels A-O show maps of the plasmid vectors referred to in FIG. 1 that were used to generate YGLY3159.
Figure 2B:
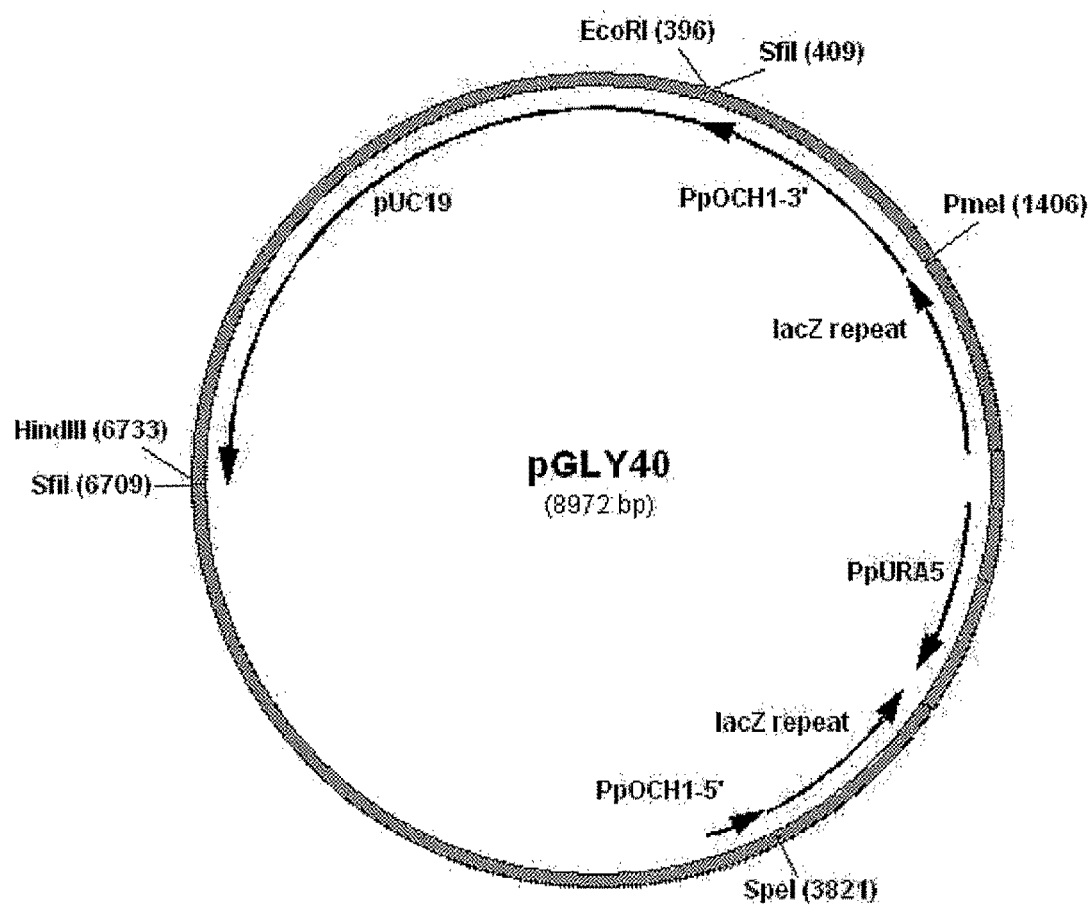
Figure 2C:
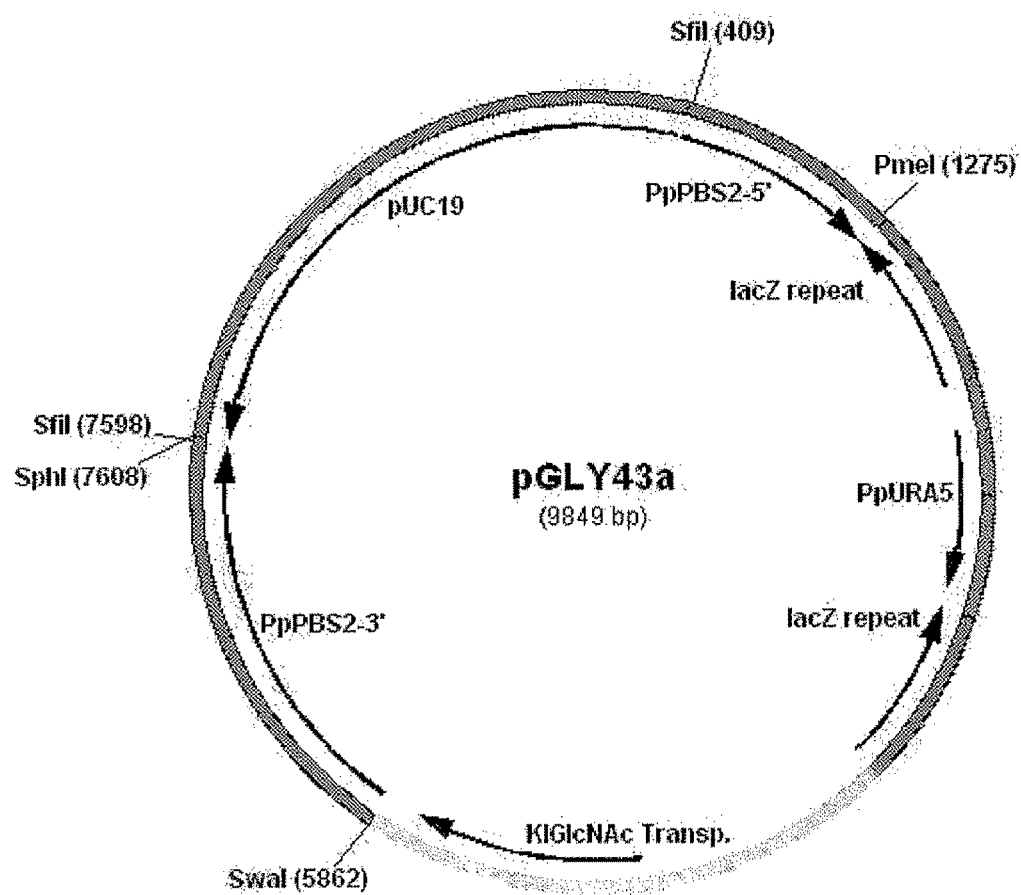
Figure 2D:
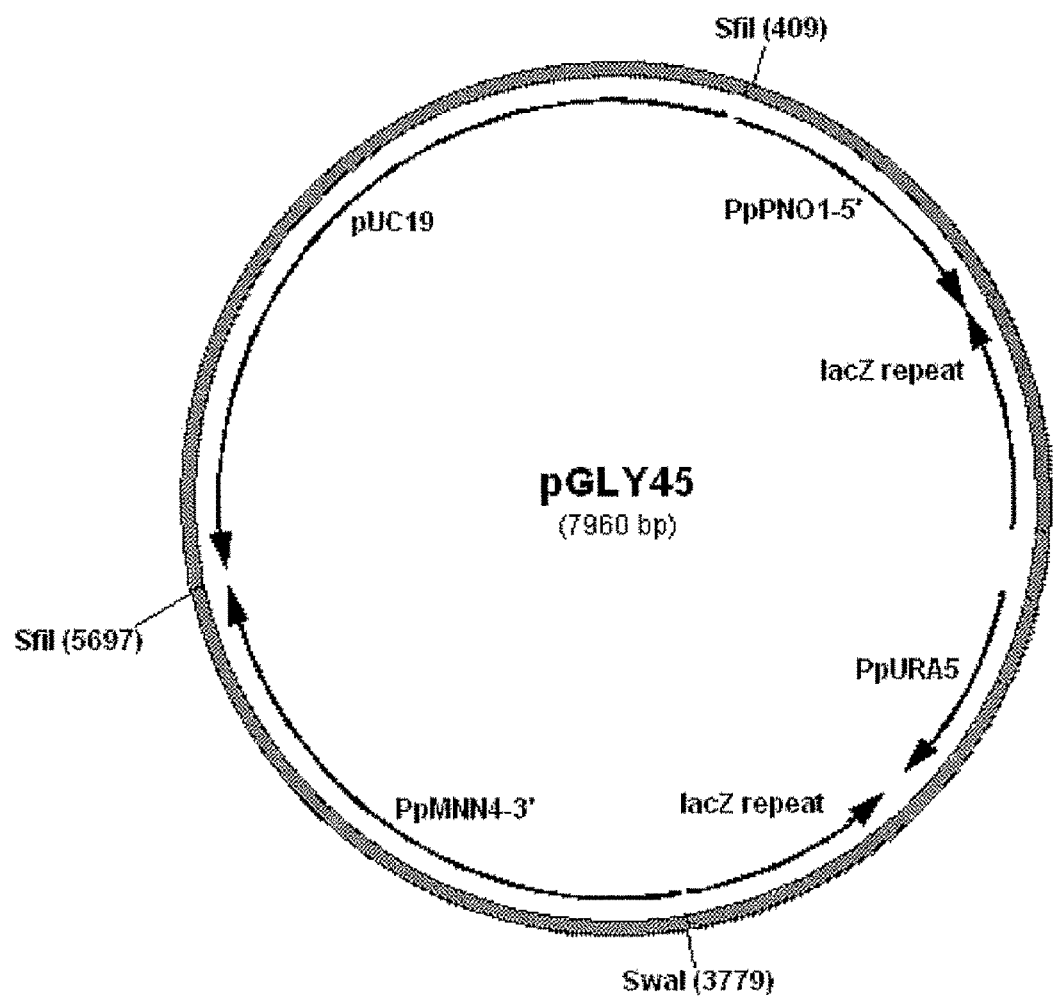
Figure 2E:
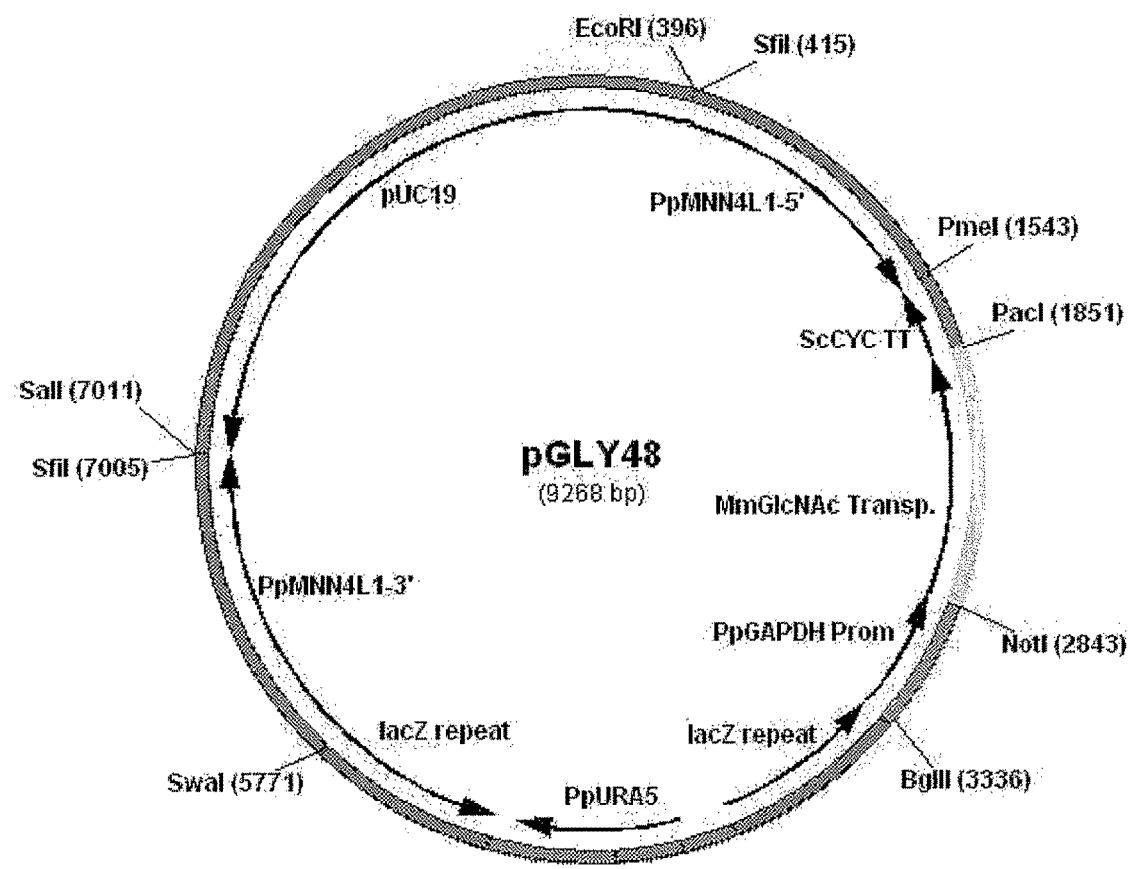
Figure 2F:
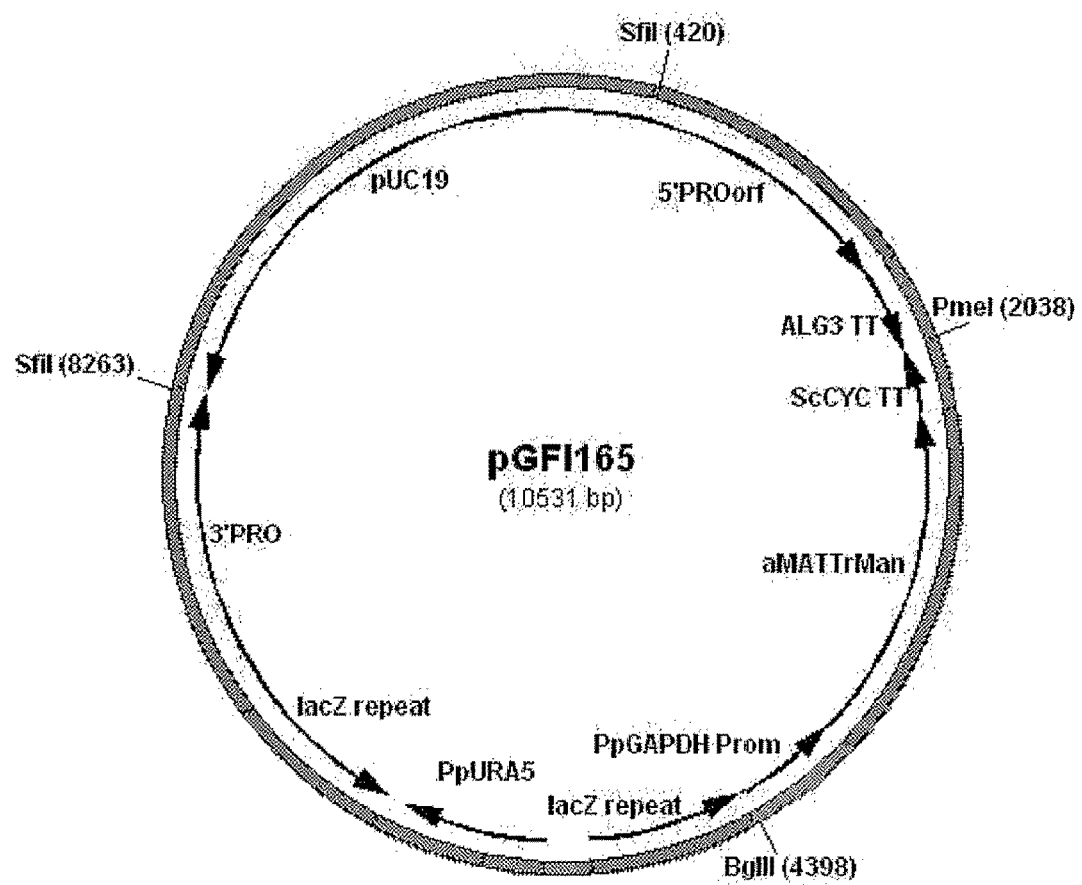
Figure 2G:
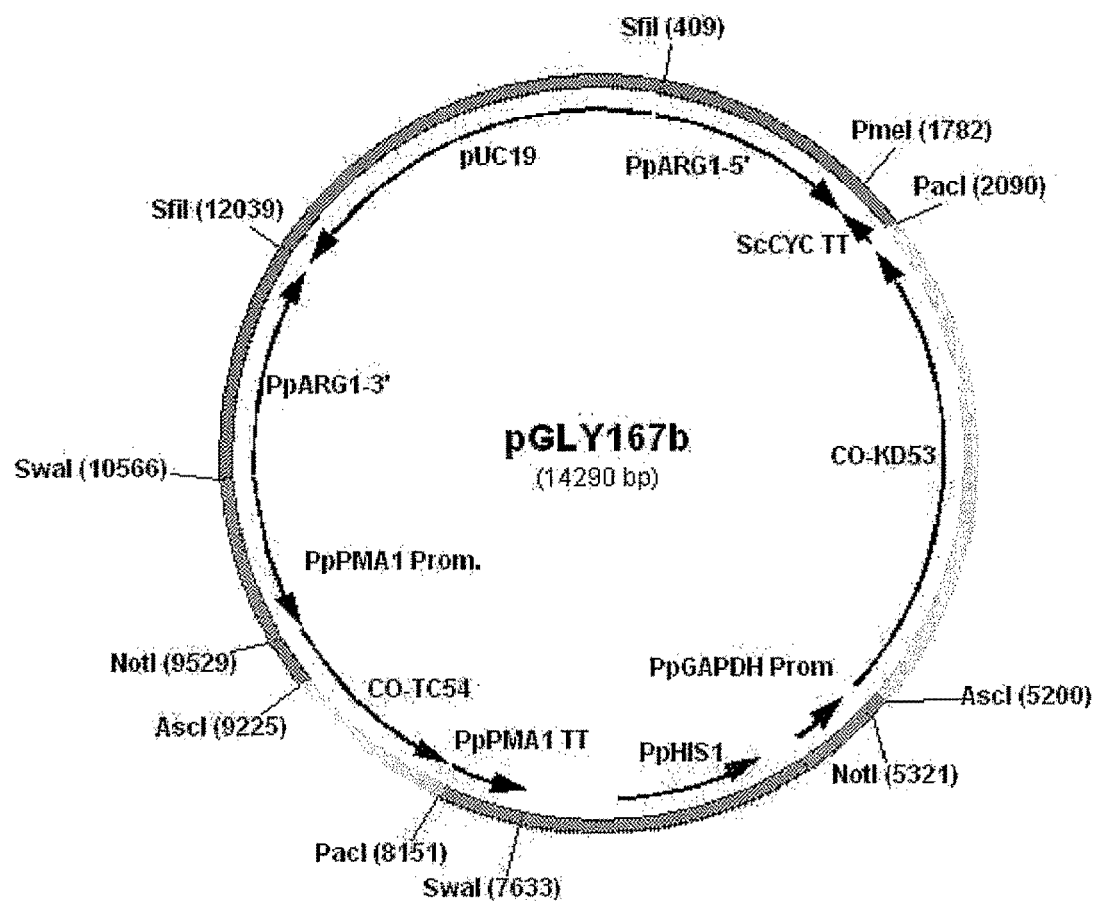
Figure 2H:
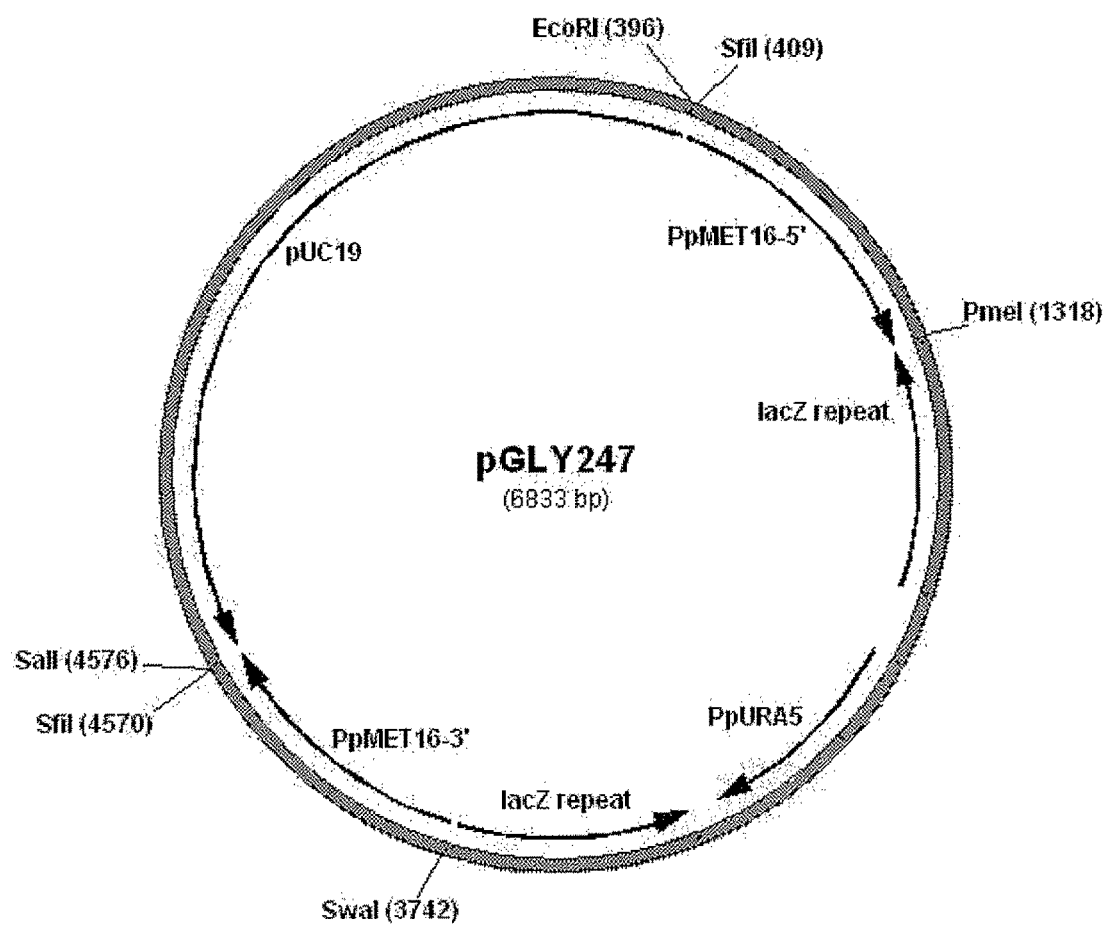
Figure 2I:
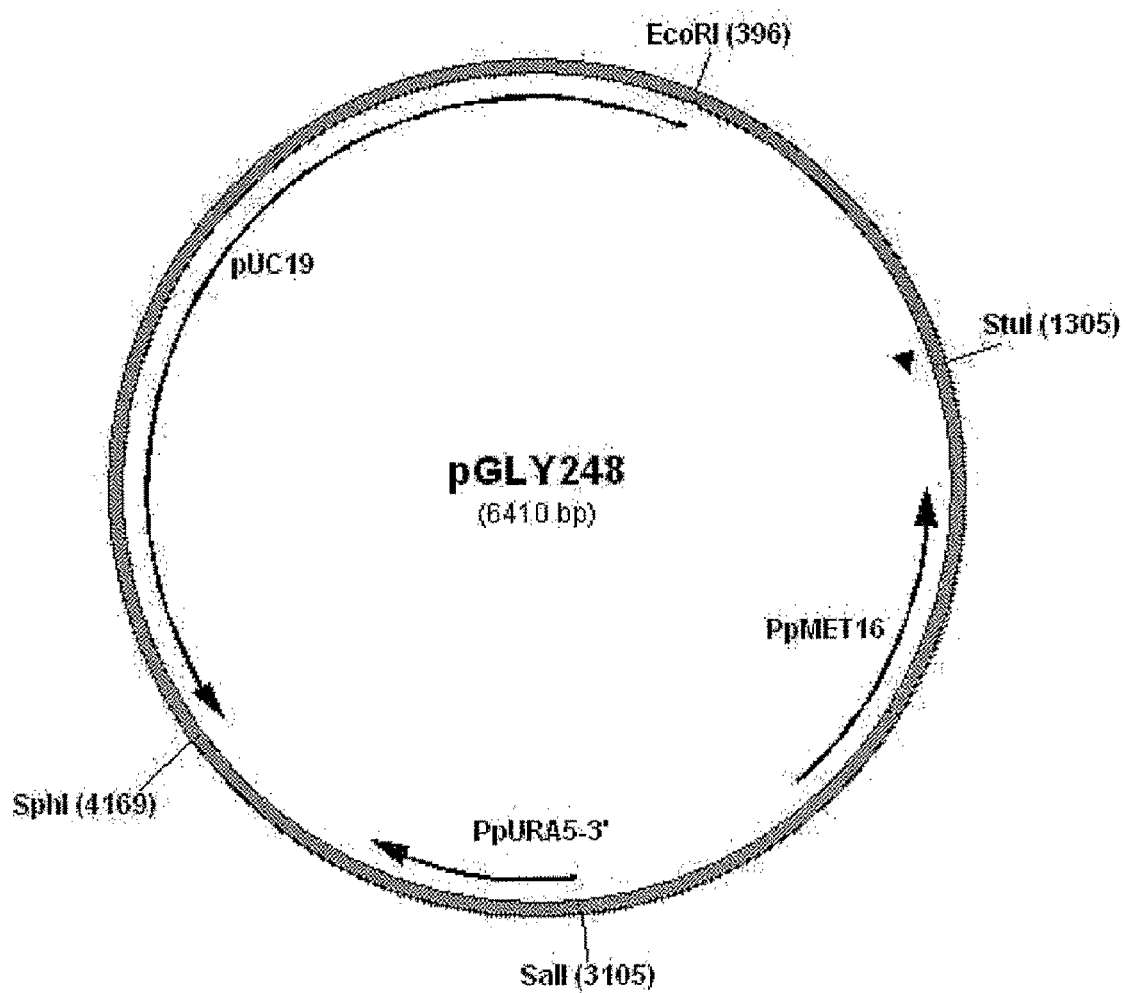
Figure 2J:
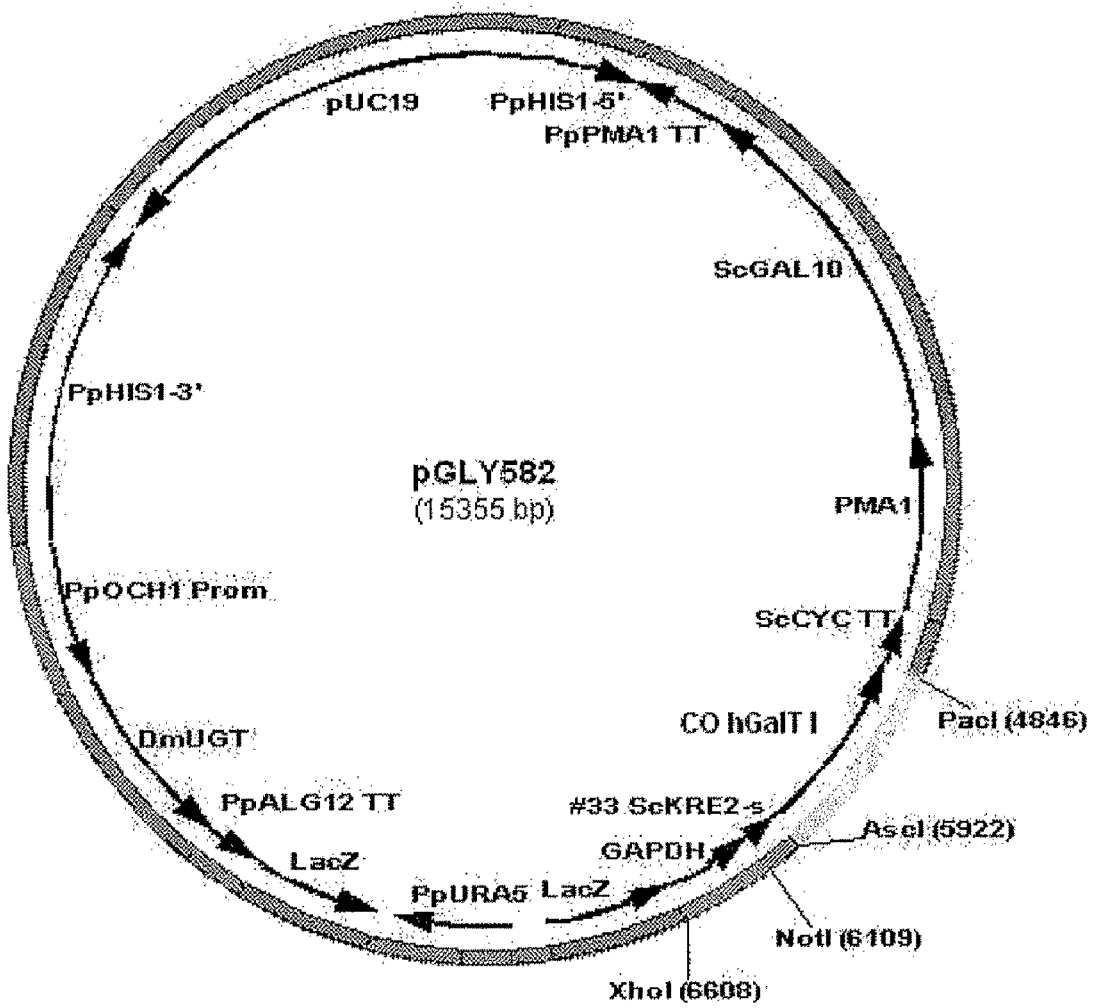
Figure 2K:
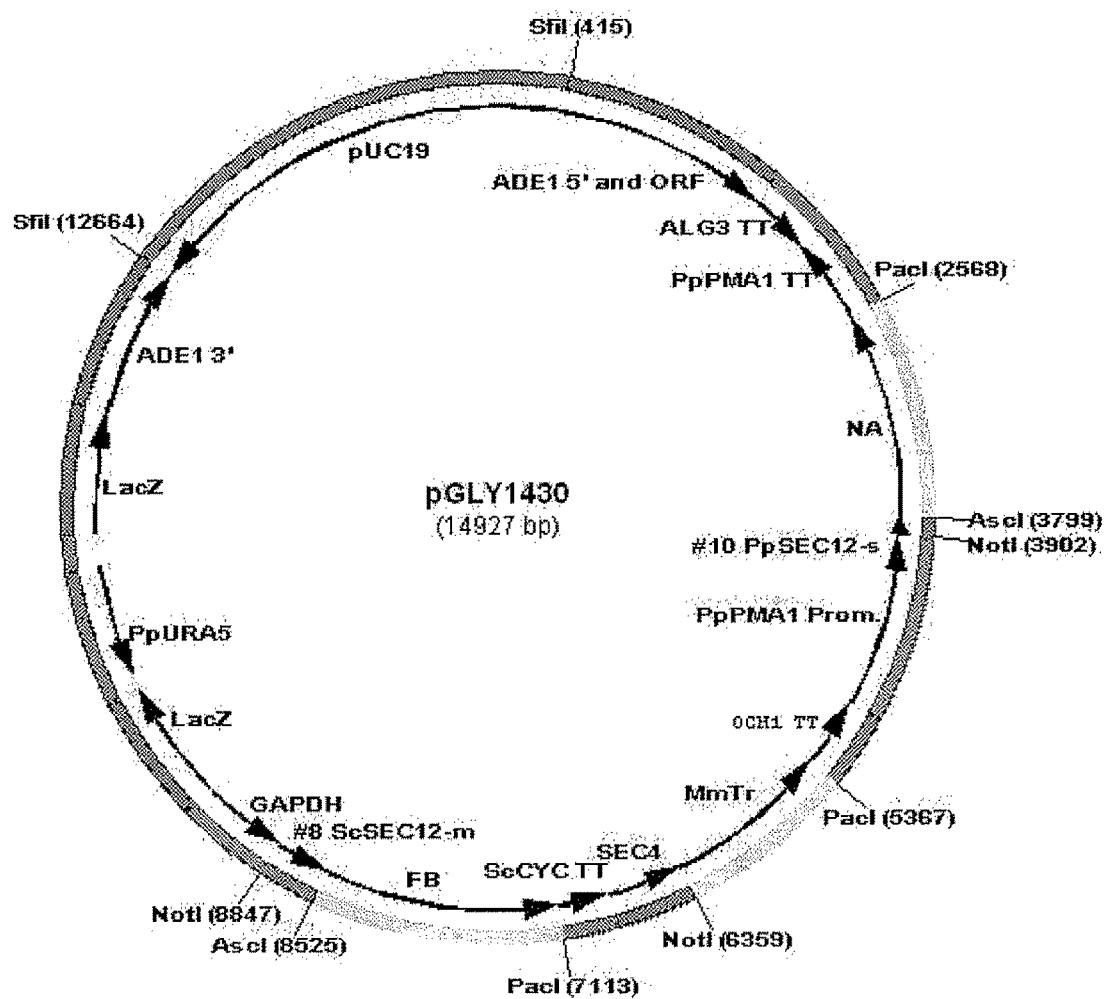
Figure 2L:
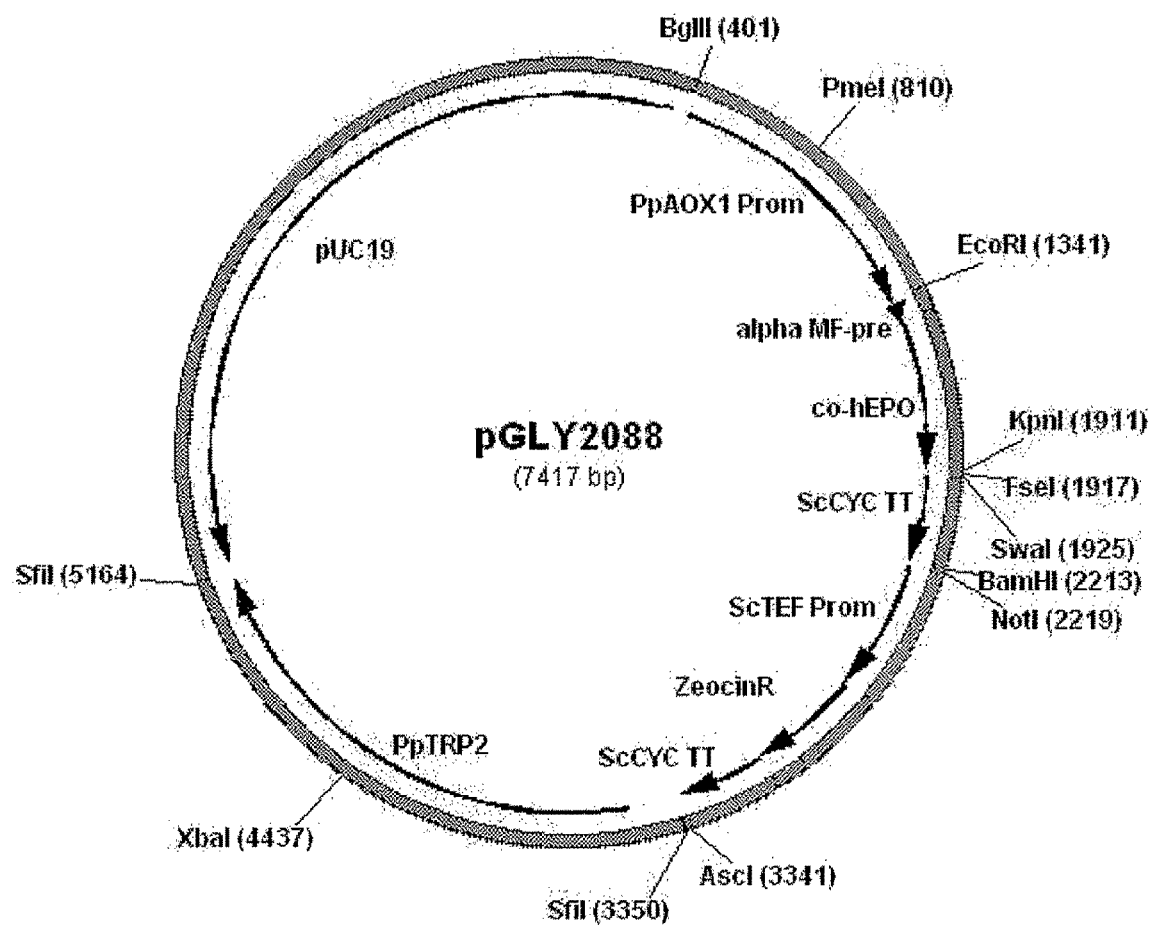
Figure 2M:
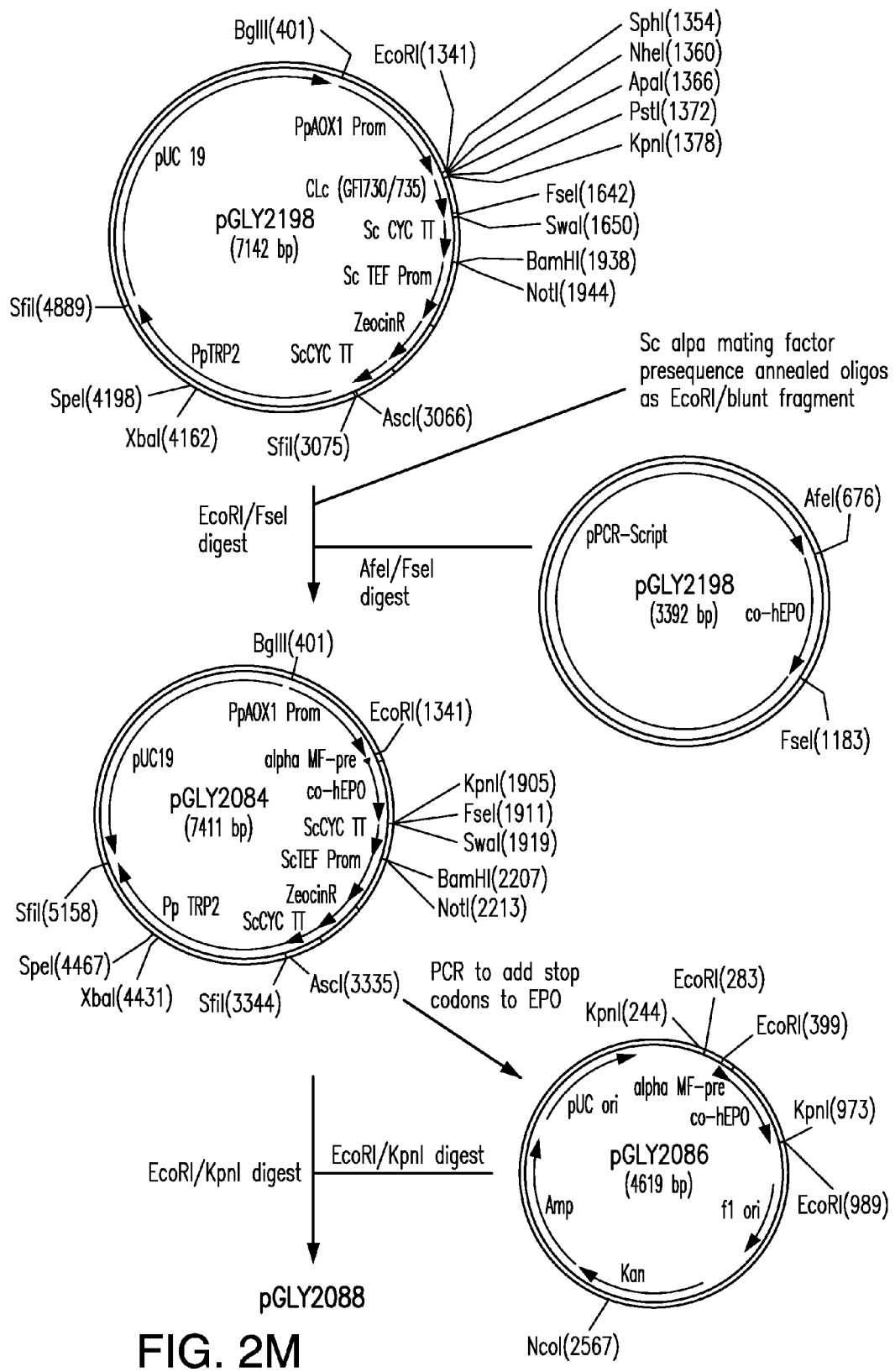
Figure 2N:
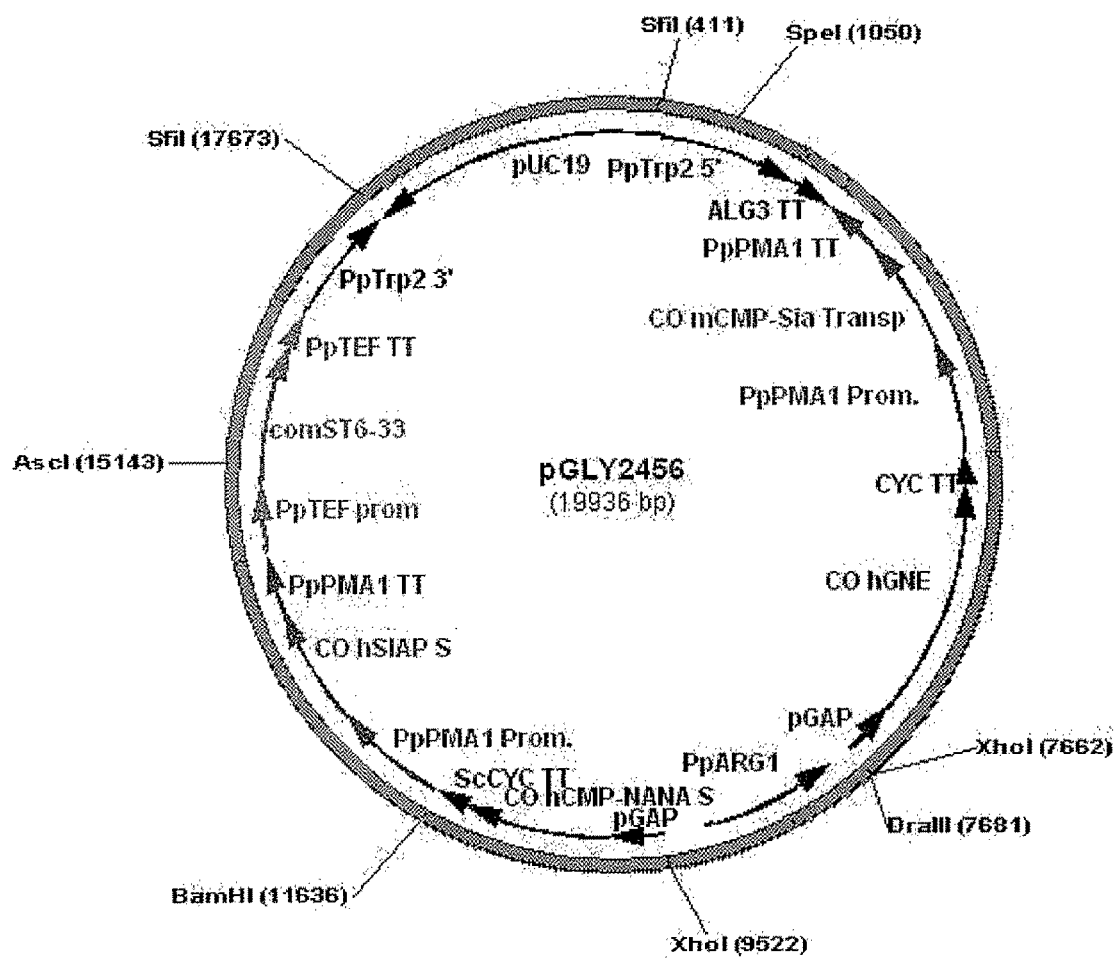
Figure 2O:
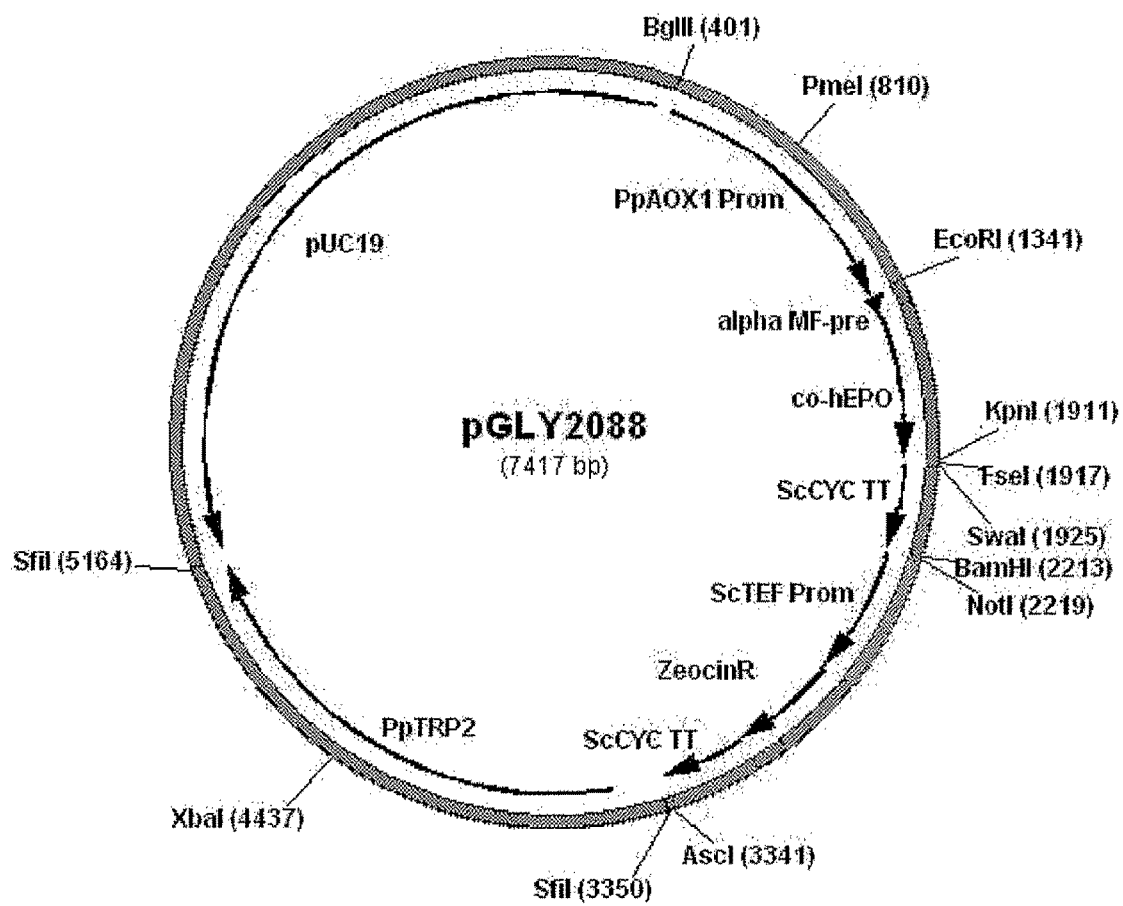

Oligos to the alpha mating factor presequence from *Saccharomyces cerevisiae* were phosphorylated and annealed to create an EcoRI overhang at the 5' end and a blunt end at the 3' end. This oligo pair was then ligated to the coding DNA sequence encoding human erythropoietin, as shown in FIG. 2, to form pGLY2088, which was transformed into *Pichia pastoris* as shown in FIG. 1.

Example 3

Transformation and Fermentation of the 6.0 Cell Line

A. Transformation

Yeast strains were transformed by electroporation (using standard techniques as recommended by the manufacturer of the electroporator BioRad).

B. Fermentation Process Description

Fermentation runs were carried out in 15 L (12 L working volume) autoclavable glass bioreactors from Applikon. The reactor is inoculated (0.04% v/v) with an exponential phase shake flask culture grown from a frozen stock vial. The batch phase ends in 24-36 hours upon depletion of the initial charge glycerol. The wet cell weight (WCW) after the batch phase is typically 120±25 g/L WCW. At this point a 50% w/w glycerol solution containing 12 mL/L PTM1 salts is fed to the fermenter in a single pulse leading to a final glycerol concentration of 30 g/L at the start of the glycerol fed-batch phase. A solution containing a synthetic inhibitor of fungal O-glycosylation (PMTi-3) dissolved in methanol at 2.6 mg/mL is added at 1 mL/L. A protease inhibitor cocktail (45 mg/mL Pepstatin A and 15 mM of Chymostatin in DMSO) is added at 0.6 mL/L. Within 4 hours the glycerol is consumed and the wet cell weight has reached 225±25 g/L WCW. Gene expression is then induced by the initiation of a methanol feed containing 12 mL/L of PMT1 salts at 2.3 g/h/L. At the start of the methanol feed batch phase as well as every 24 hours of induction, 1 mL/L of 2.6 mg/mL PMTi-3 in methanol and 0.6 mL/L of the protease inhibitor cocktail are added. Induction continues for 40 hours when the final wet cell weight is expected to be approximately 300±25 g/L. (L* is the initial charge volume before inoculation).

Primary clarification of fermentor broth is performed by centrifugation. The whole cell broth is transferred into 1000 mL centrifuge bottles and centrifuged at 4° C. for 15 minutes at 13,000×g.

Example 4

Purification

Figure 3:
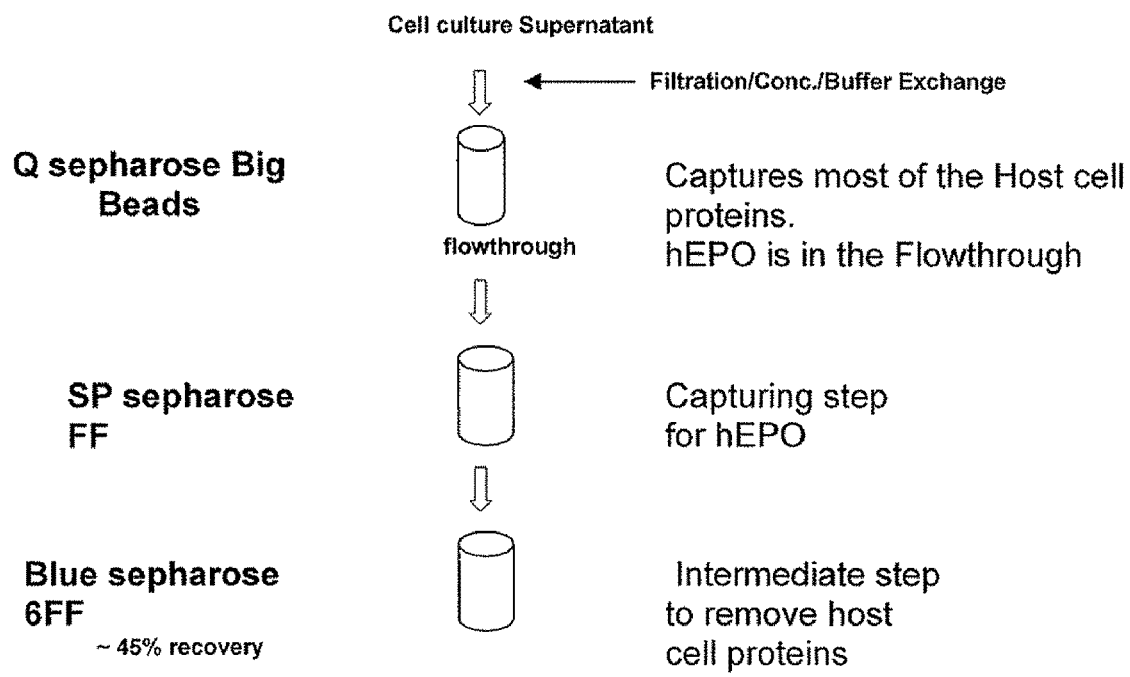
FIG. 3 illustrates a three-step chromatographic separation process used to purify human EPO.
Figure 4A:
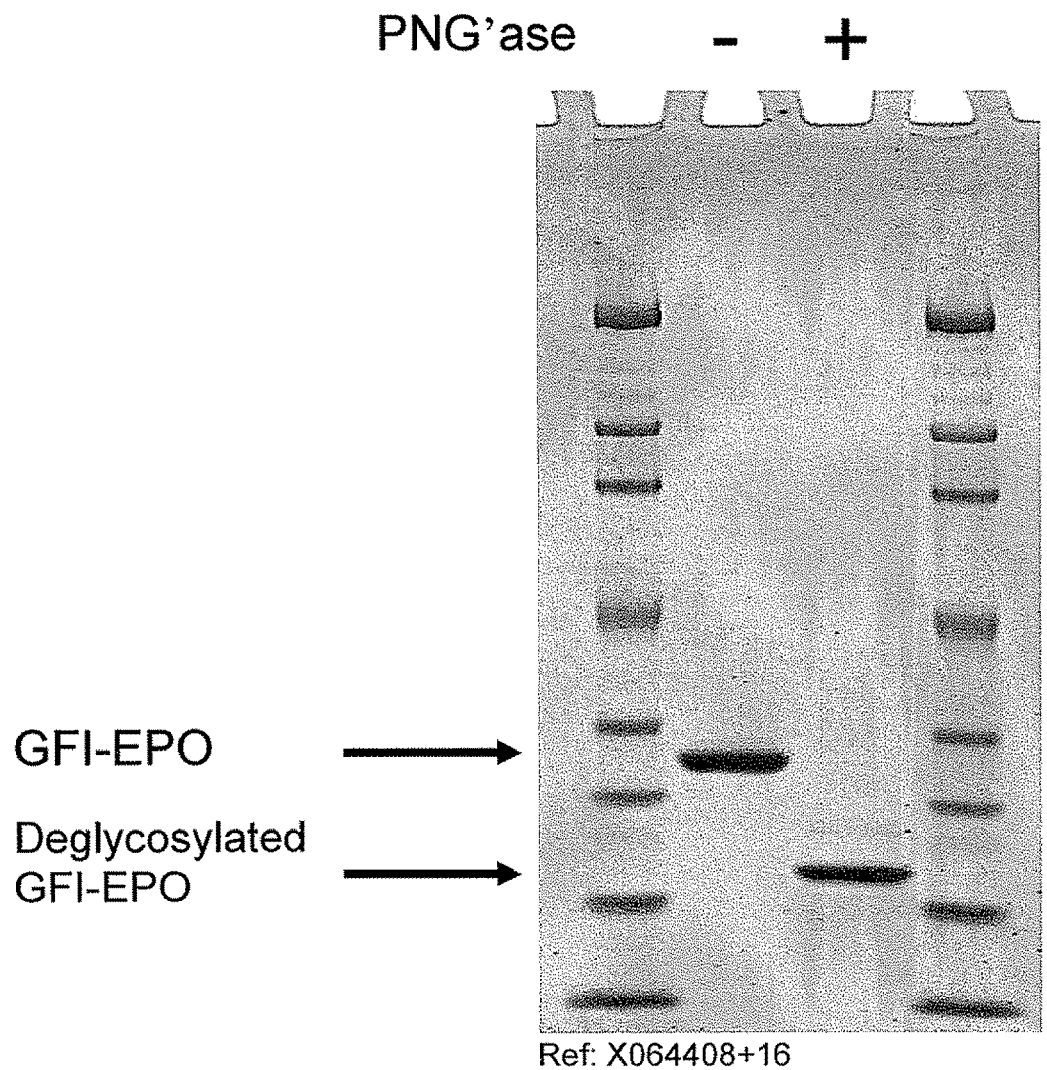
FIGS. 4A-4D shows the characterization of purified EPO by Panel 4A) SDS-PAGE, showing overall purity of sample Panel 4B) size exclusion chromatography (SEC-HPLC) showing a uniform single peak demonstrating the lack of degradation and lack of aggregation Panel 4C) reverse phase (RP)-HPLC demonstrating intactness of EPO and Panel 4D) LC-MS demonstrating product quality on PNGase F treated EPO.
Figure 4B:
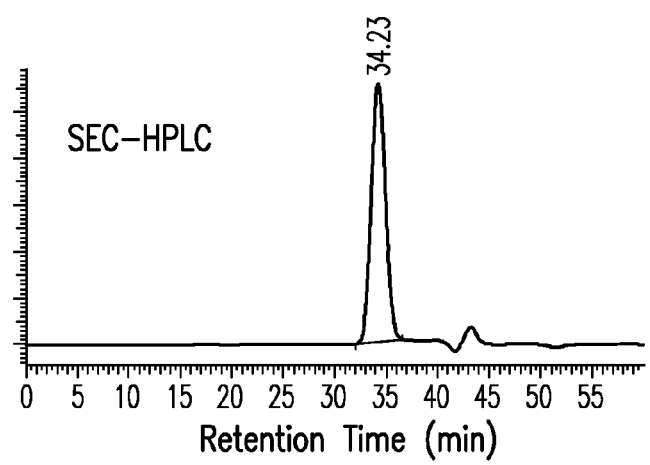
Figure 4C:
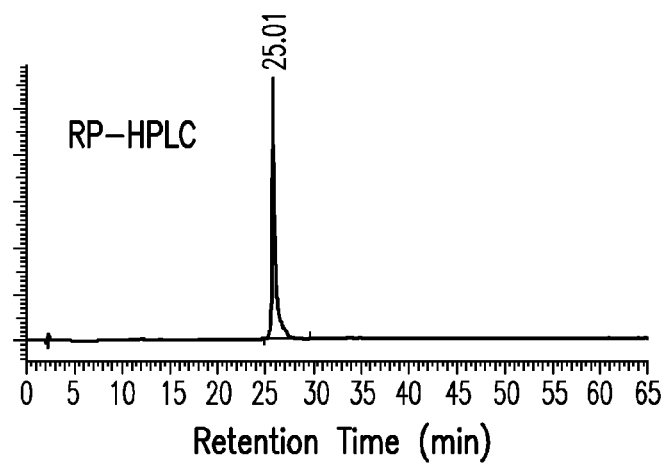
Figure 4D:
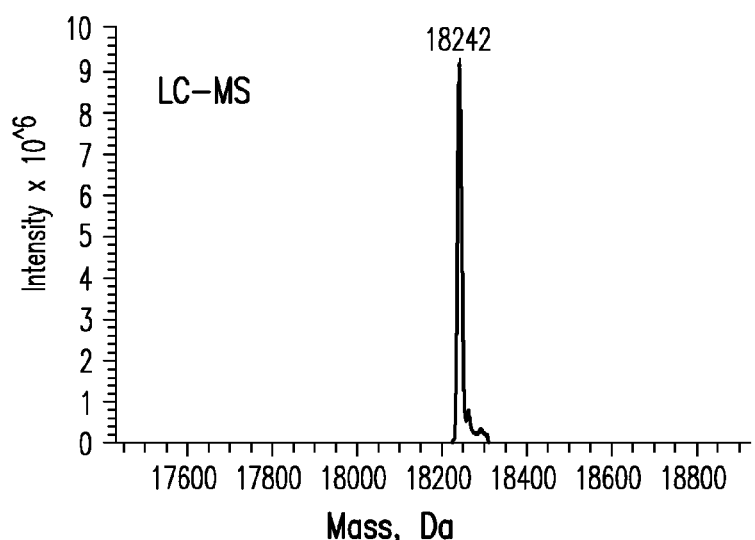

Human EPO (hEPO) for PEGylation was generated by a three-step chromatographic separation, as follows, in which 95% purity was achieved (FIG. 3). First, cell-free fermentation supernatant was filtered through 0.2 μm membrane filter, concentrated and buffer exchanged using a MiniKross tangential flow separation module with hollow fiber membrane.

Q sepharose Big Beads were used in the first step to capture the host cell proteins and hEPO flowthrough. The pool of flowthrough and the wash samples from the Q sepharose Big Beads column were adjusted to pH 5.0 with acetic acid. Conductivity was measured to ensure a value of approximately 4.5 mS/cm.

Next, the sample was filtered through a 0.2 μm membrane filter and loaded on to a SP sepharose Fast Flow column pre-equilibrated with three column volumes of 50 mM sodium acetate pH 5.0. Ten column volumes of a gradient from 50 mM sodium acetate pH 5.0 to 20 mM sodium acetate pH 5.0; 500 mM NaCl was applied to elute the protein, followed by a step elution with 0.5 column volumes 20 mM sodium acetate pH 5.0; 750 mM NaCl. Fractions containing hEPO were pooled and dialyzed in 50 mM TRIS pH 7.0.

The hEPO containing fractions were loaded on to a Blue Sepharose 6 FF column pre-equilibrated with three column volumes of 50 mM TRIS pH 7.0, Ten column volumes of a linear gradient from 50 mM TRIS pH 7.0 to 50 mM TRIS pH 8; 3M NaCl were applied, followed by a step elution of two column volumes with 50 mM TRIS pH 8; 3M NaCl.

The fractions that displayed an EPO band (average molecular weight ~25 kDa) were pooled, filtered through a 0.2 μm membrane filter, dialyzed in 20 mm MES pH 6.0 at 4° C. and stored at 4° C. The sample pool was then concentrated and dialyzed in 50 mM sodium acetate buffer at pH 5.2 to a protein concentration of 1 mg/ml.

It has been seen that exposure of fermentation supernatant to pH 5 increased the loss of hEPO. It is therefore important to maintain the capture and intermediate step of hEPO purification at neutral pH.

Figure 10:
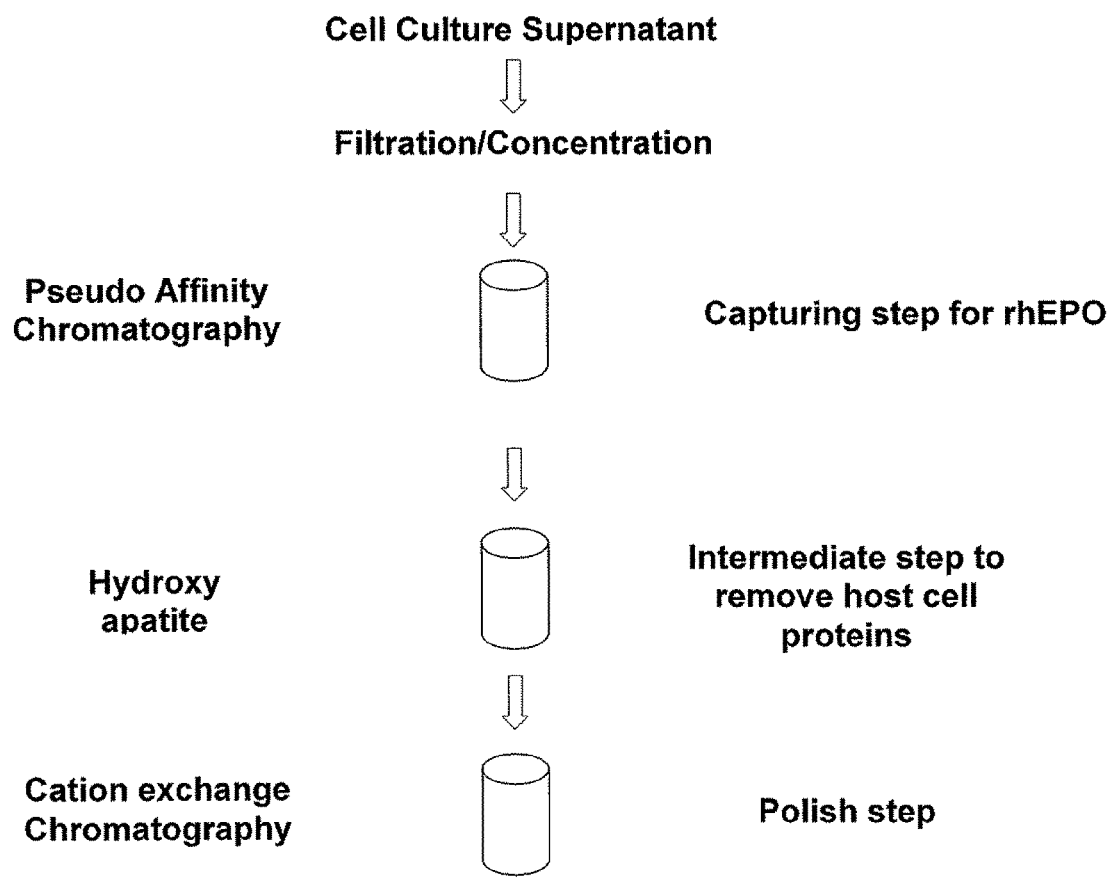
FIG. 10 shows a overview of a purification strategy for recombinant human EPO.
Figure 11:
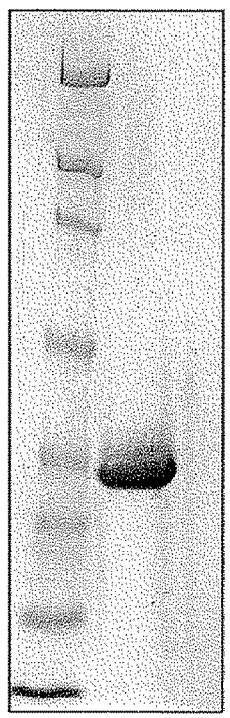
FIG. 11 shows a Coomassie stained gel of purified recombinant human EPO.

An overview of a second general purification scheme is shown in FIG. 10. A purified sample prepared using this scheme was analyzed by SDS-PAGE shown in FIG. 11.

Primary clarification is performed by centrifugation. The whole cell broth is transferred into 1000 mL centrifuge bottles and centrifuged at 4° C. for 15 minutes at 13,000×g. An ultrafiltration step can be employed for larger fermentors (10 L to 40 L and larger). This step can be performed utilizing Sartoriuos flat sheets with a pore size of 10K to a 5 fold concentration.

A capture step is performed with a Blue Sepharose 6 fast flow (GE healthcare) equilibrated with 50 mM Tris-HCl/100 mM NaCl, pH 7. The supernatant was adjusted to 100 mM NaCl and passed through dead-end filter (Whatman, Polycap TC) before loading to the column. The residence time is maintained to 10 min with a 3 column volumes (CV) wash after loading. The elution is performed in steps of 2 CV with 250 mM and 3 CV with 1M NaCl. EPO elutes at the 1 M NaCl.

Macro-prep ceramic hydroxyapatite Type 140 μm (Bio-Rad) is used after the capture step. This column is equilibrated with 50 mM MOPS containing 1M NaCl and 10 mM CaCl2 pH 7. 10 mM CaCl2 is added to the pooled EPO from the blue column before loading. The column wash is executed with 3 CV of equilibration solution followed by 10 CV linear gradient from 0 to 200 mM Na phosphate pH 7. EPO elutes between 60 mM and 100 mM Na phosphate.

Source 30S (GE Healthcare) can be used as an optional purification step. If this is the case, the pooled sample after hydroxyapatite is dialyzed against 50 mM NaAcetate pH 5 overnight at 4° C. and the column is equilibrated with the same buffer. A 10 CV linear gradient from 0 to 750 mM NaCl is applied with EPO elutioning in between 350 to 500 mM NaCl.

Purified EPO Analysis

N-glycans were released from the purified EPO by treatment with PNGase F (Choi PNAS, Hamilton 2003 Science) and analyzed by SDS-PAGE according to Laemmli (Laemmli 1970) (FIG. 4).

The intactness and presence of aggregation of the purified EPO was determined by size exclusion chromatography (SEC-HPLC) using a Hitachi D7000 instrument with L7420 UV detector monitoring 280 nm, a Wyatt miniDAWN three-angle light scattering detector detecting at 690 nm, a Wyatt Optilab rEx differential refractive index detector detecting at 690 nm, a GE Healthcare Superdex 200 10/300 GL column (#17-5175-01), and Wyatt ASTRA V 5.3.1.5 software (FIG. 4A-4D).

Ninety microliters of sample (>0.1 mg/ml) is placed in a sample vial, capped and then injected into the column. The HPLC gradient consists of a 60 minute isocratic run at room temperature with a flow rate of 0.45 ml/min using a buffer of 100 mM sodium phosphate (pH 6.8), 150 mM NaCl, and 0.05% sodium azide.

Molecular weights are calculated using a protein conjugate analysis module of ASTRA software. The differential refractive index detector is set to the concentration detector. A dn/dc of 0.185 ml/g is used for protein and 0.136 ml/g for PEG and glycans.

The purity of purified EPO was quantified by RP-HPLC using a Hitachi D7000 HPLC instrument with L-7455 diode array detector and a Jupiter 5μ, C4 300 Å 150 mm×4.6 mm ID column (#00E-4167-E0, Phenomenex) (FIG. 4). Ninety microliters is injected and the sample is monitored at 280 nM and separated according to the gradient below (column oven is pre-heated to 80° C.) with the following buffers:

Buffer A: 0.1% trifluoroacetic acid (TFA) in HPLC-grade water sparged with helium gas
Buffer B: 0.08% TFA in HPLC-grade acetonitrile sparged with helium gas

TABLE 2

| Time (min) | Flow rate (ml/min) | Buffer A (%) | Buffer B (%) |
|---|---|---|---|
| 0 | 1 | 95 | 5 |
| 1 | 1 | 95 | 5 |
| 58 | 1 | 0 | 100 |
| 64.9 | 1 | 0 | 100 |
| 65 | 1 | 95 | 5 |
| 70 | 1 | 95 | 5 |

The quality of the hEPO protein was evaluated and post-translational modifications were assessed by peptide mapping (LC-MS) using an Advion Triversa Nanomate, a Thermo Electron Finnigan LTQ mass spectrometer, a Thermo Electron Finnigan Surveyor HPLC system, a Jupiter 4μ Peoteo 90A column, 250×4.60 mm (#00G-4396-E0, Phenomenex), and a spin column with a 10 kDa molecular weight cutoff (VS0101, Vivascience) (FIG. 7), A 100 μl sample (>1 mg/ml) is placed in a 1.5 ml Eppendorf tube, 150 μl 10M GuHCl and 2.5 μl 1 M Dithiothreitol (DTT) are added. The sample contents are mixed and the sample is incubated for 1 hr at 37° C. The sample is allowed to cool at room temperature and 10 μl 1M Iodoacetic acid (IAA) is added. Light is avoided by wrapping the sample tubes with aluminum foil and the samples are incubated at room temperature for 45 min. The sample buffer is exchanged to 25 mM ammonium bicarbonate ($NH_4HCO_3$) pH7.8 (6 times for 10-fold dilution each time), and the final volume is reduced to ~30 μl. 1 μg trypsin stock solution (constitute lyophilized trypsin in 50 mM acetic acid at 1 μg/μl and aliquot 20/tube, store at −20° C.) and acetonitrile to 5% (v/v) are added. The reaction solution is placed at 37° C. and incubated overnight (~16 hours). MALDI-TOF analysis is performed to ensure completion of the trypsin digest and the trypsin activity is inactivated. Formic acid is then added to a final concentration of 0.1% (v/v) to bring the pH down. Fifteen microliters of the digest is mixed with 15 μl HPLC buffer A (0.1% formic acid (FA) in HPLC-grade water) and loaded into a sample vial. The HPLC setup is as follows:
1) Sample tray temperature: 4° C.;
2) Column oven temperature: 30° C.;
3) Partial loop injection;
4) UV detection: 215 nm and 280 nm;
5) HPLC gradient:

TABLE 3

| Time (min) | Flow rate (ml/min) | Buffer A (%) | Buffer B (%) |
|---|---|---|---|
| 0 | 1 | 98 | 2 |
| 70 | 1 | 65 | 35 |
| 80 | 1 | 2 | 98 |
| 85 | 1 | 2 | 98 |
| 86 | 1 | 98 | 2 |
| 90 | 1 | 98 | 2 |

The mass spectrometer setup is as follows:
1) Flow to LTQ ~400nl/min through Advion Triversa Nanomate;
2) Capillary temperature: 115° C., capillary voltage: 5 v; tube lens voltage: 77v
3) Scan set for neutral loss top 3 to MS4 for 90 min.

The chromatogram is plotted by looking at the base peak trace from the mass detector. The peptides present in each peak are identified by searching the hEPO sequence using Sequest software as well as manual inspection.

Example 5

Description of the PEG Molecules and Process Used for PEGylation

Figure 5:
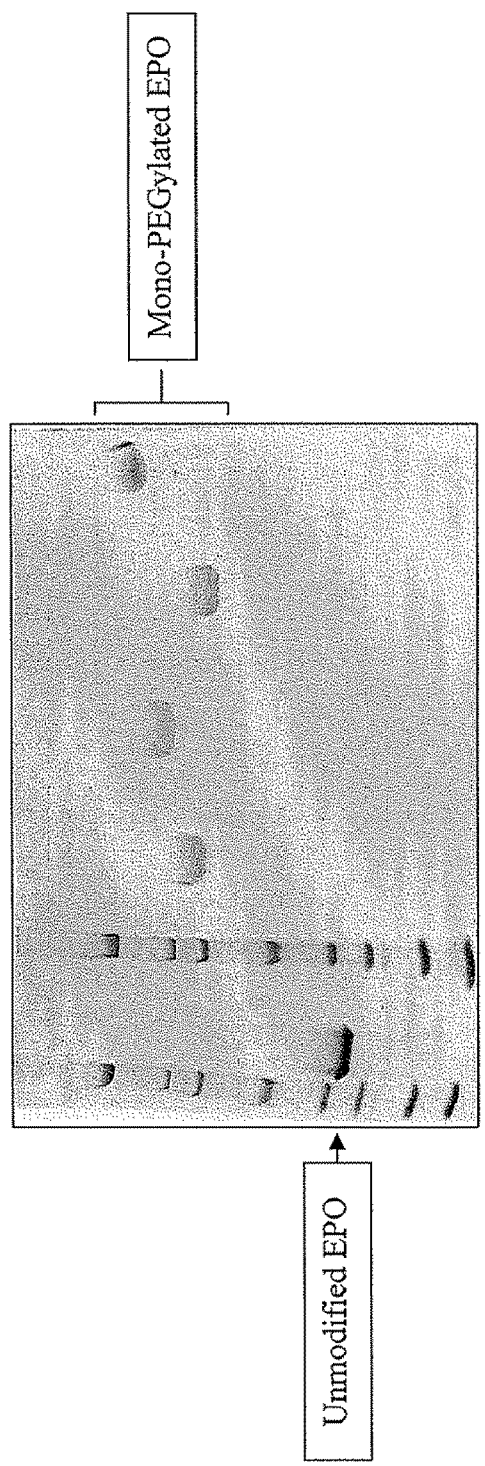
FIG. 5 shows SDS PAGE analysis of the purified hEPO sample conjugated to a 30 kDa, 40 kDa, or 60 kDa linear PEG or a 45 kDa branched PEG.
Figure 6:
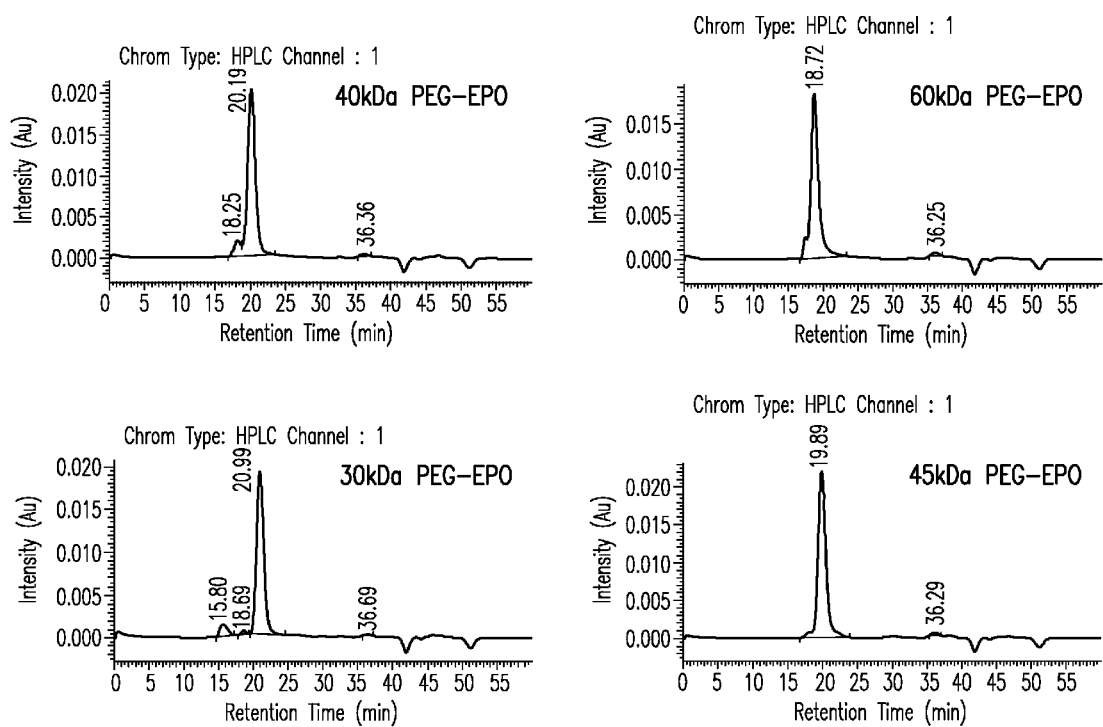
FIG. 6 shows size exclusion chromatography (SEC HPLC) analysis of four different PEGylated EPO products.

The following PEG molecules were used for PEGylation of hEPO:
40 kDa linear methoxy poly(ethylene glycol) proprionaldehyde from Dow (Cambridge, UK)
60 kDa linear methoxy poly(ethylene glycol) proprionaldehyde from Dow (Cambridge, UK)
30 kDa linear α-methyl-ω-(3-oxopropoxy), polyoxyethylene from NOF Corporation (Tokyo, Japan)
45 kDa branched 2,3-Bis(methylpolyoxyethylene-oxy)-1-[(3-oxopropyl)polyoxyethylene-oxy]-propane from NOF corporation The different activated PEGs (30 kDa, 40 kDa, or 60 kDa linear PEGs or 45 kDa branched PEG) were added to the hEPO sample (conc. 1 mg/mL) in 50 mM Sodium acetate buffer at pH 5.2 at a protein:PEG ratio of 1:10. The reaction was carried out at room temperature under reducing conditions by adding 10 mM sodium cyanoborohydride to the reaction mixture with overnight stirring. The reaction was stopped by adding 10 mM TRIS. Mono-PEGylated hEPO was purified using a SP sepharose Fast Flow column and analyzed by SDS-PAGE (FIG. 5).

If further optimization is desired, the following parameters can be examined:
1) Different pH ranges (pH 4.0, 4.5, 5.2 and 6.0)
2) Different molar ratio of hEPO:mPEG-aldehyde (1:5, 1:10, 1:20)
3) Room temperature versus 4° C.
4) Different types of PEGs Example 6

Characterization of the PEGylated EPO Products

The four different PEGylated EPO products were analyzed by SEC HPLC (FIG. 6) as described in Example 4. For quantitation of N-linked glycan structures (FIG. 7), N-linked glycans were released from the PEGylated EPO by treatment with PNGase-F (Choi PNAS, Hamilton 2003 Science) and labeled with 2-aminobenzidine (2-AB) using a commercial 2-AB labeling kit. HPLC was performed using a Prevail CHO ES, 5 micron bead, amino-bound silica column maintained at 30° C. The elution profile is as follows (Solvent A: 100% acetonitrile, Solvent B: 50 mM ammonium formate pH 4.4):

TABLE 4

| Time/min | Flow rate (ml/min) | % A | % B |
|---|---|---|---|
| 0 | 1 | 80 | 20 |
| 30 | 1 | 40 | 60 |
| 60 | 1 | 0 | 100 |
| 65 | 1 | 0 | 100 |
| 70 | 1 | 80 | 20 |
| 80 | 1 | 80 | 20 |

Figure 7:
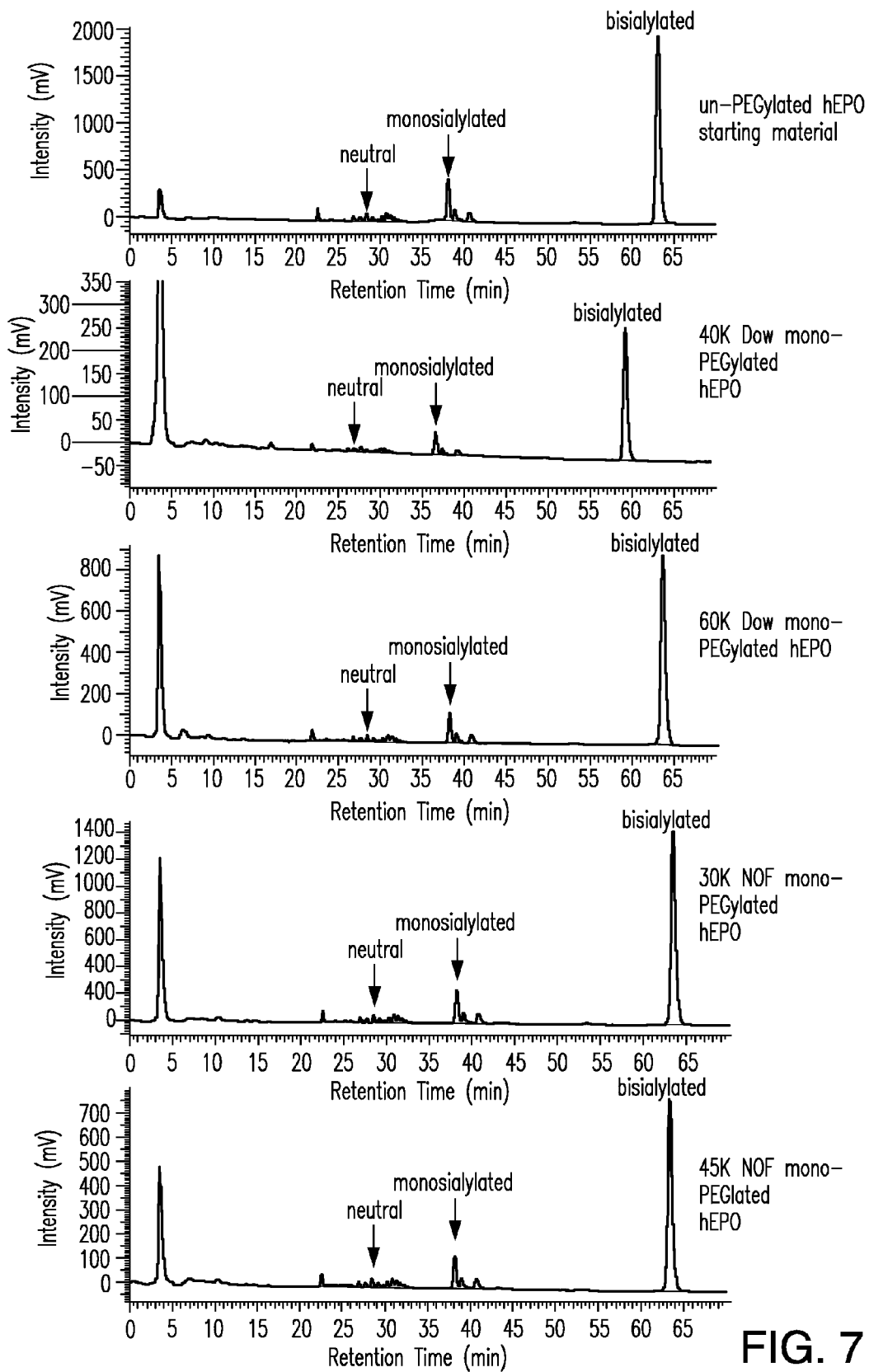
FIG. 7 shows high performance liquid chromatograms of the N-linked glycans released from unPEGylated EPO and four different PEGylated EPO products by treatment with PNGase-F and labeled with 2-aminobenzidine (2-AB) The chromatograms demonstrate the predominance of the bisialylated glycoform $GlcNAc_2Man_3GlcNAc_2Gal_2NANA_2$.

FIG. 7 shows that approximately 70-74% of the PEGylated EPO products in the tested samples are bisialylated (see the last peak in each panel).

Example 7

Formulation

A representative formulation of PEG-EPO may be 20 mM sodium phosphate, 140 mM sodium chloride, 0.005% Polysorbate 80, pH 6.0, which is based on a similar marketed erythropoietin product. PEG-EPO can be formulated for injection as a sterile, clear liquid, at multiple potencies, and dispensed in single dose glass vials ranging in concentration from 25-500 µg/mL. As these concentrations are in the low range, there is concern regarding protein adsorption to the vial, which could result in loss of dose. To minimize adsorption, surfactants are usually added to formulations (i.e., Polysorbate 20, Polysorbate 80) at limited concentrations. The need for surfactant will be based on material compatibility studies conducted during formulation development.

Other Formulations of Commercial EPOs

Commercial formulations of erythropoietin are known and my be adapted for use with the erythropoietins of the present invention. Some examples of commercial EPO formulations are as follows:

ARANESP®: Polysorbate solution: Each 1 mL contains 0.05 mg polysorbate 80, and is formulated at pH 6.2±0.2 with 2.12 mg sodium phosphate monobasic monohydrate, 0.66 mg sodium phosphate dibasic anhydrous, and 8.18 mg sodium chloride in water for injection, USP (to 1 mL).

Albumin solution: Each 1 mL contains 2.5 mg albumin (human), and is formulated at pH 6.0±0.3 with 2.23 mg sodium phosphate monobasic monohydrate, 0.53 mg sodium phosphate dibasic anhydrous, and 8.18 mg sodium chloride in water for injection, USP (to 1 mL).

EPOGEN® is formulated as a sterile, colorless liquid in an isotonic sodium chloride/sodium citrate buffered solution or a sodium chloride/sodium phosphate buffered solution for intravenous (IV) or subcutaneous (SC) administration.

Single-dose, Preservative-free Vial: Each 1 mL of solution contains 2000, 3000, 4000 or 10,000 Units of Epoetin alfa, 2.5 mg Albumin (Human), 5.8 mg sodium citrate, 5.8 mg sodium chloride, and 0.06 mg citric acid in water for injection, USP (pH 6.9±0.3). This formulation contains no preservative. Preserved vials contain 1% benzyl alcohol.

Example 8

In Vivo Analysis of PEG-EPO

In Vivo Studies in Mice:

Mouse efficacy study: The four different versions of PEG-EPO produced in *P. pastoris* strain YGLY3159 engineered to generate bi-antennary terminally sialylated (>70%) human EPO were compared with commercial Aranesp for their ability to increase hematocrit. C57B6 mice (age 7 weeks at start of study, weight 18-20 g, 3 males/3 females per treatment group) were obtained and acclimated for one week. Hematocrit values were determined before dosing to obtain a baseline for each animal. Animals were segregated into six groups:

(1) vehicle (saline+100 µg/ml rHSA);
(2) ARANESP@2.5 µg/kg/dose (darbepoetin, albumin-free);
(3) PEG-EPO [40 kDa linear DOW]@ 2.5 µg/kg/dose;
(4) PEG-EPO [60 kDa linear DOW]@ 2.5 µg/kg/dose;
(5) PEG-EPO [30 kDa linear NOF]@ 2.5 µg/kg/dose;
(6) PEG-EPO [45 kDa branched NOF]@ 2.5 µg/kg/dose.

Figure 8:
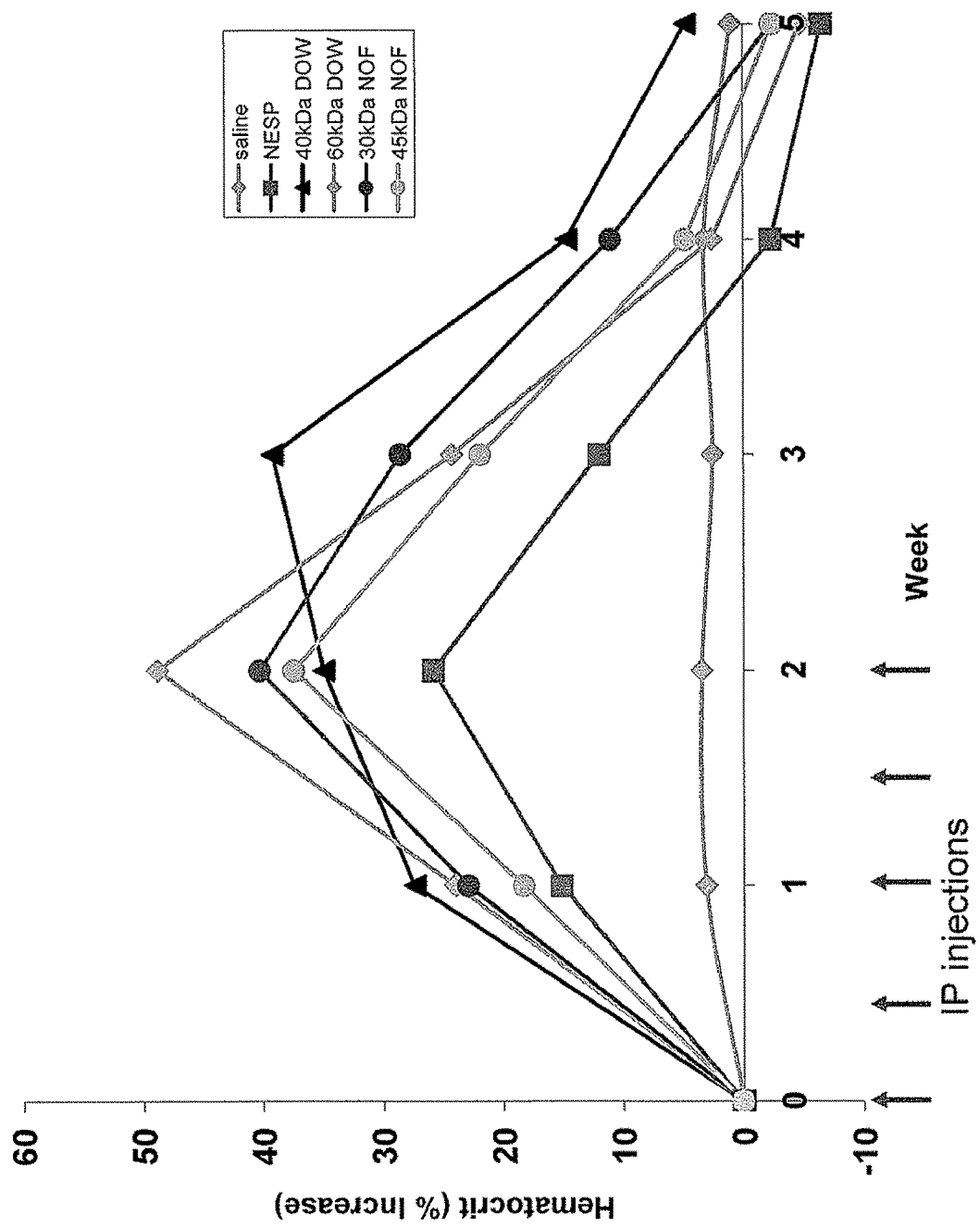
FIG. 8 shows that mice injected with four different versions of PEG-EPO conjugates display an increase in hematocrit over commercially purchased Aranesp. C57B6 mice were dosed twice weekly for a total of five injections (dosing was stopped after 2.5 weeks). The mice were bled weekly and hematocrit values were determined.

Animals were dosed by intraperitoneal injection twice weekly (Monday and Thursday) for a total of five injections (dosing was stopped after 2.5 weeks). The mice were bled weekly (Monday) and hematocrit values were determined. Mice injected with PEG-EPO conjugates of the present invention display an increase in hematocrit over commercial Aranesp. The data is presented in FIG. 8.

Figure 13:
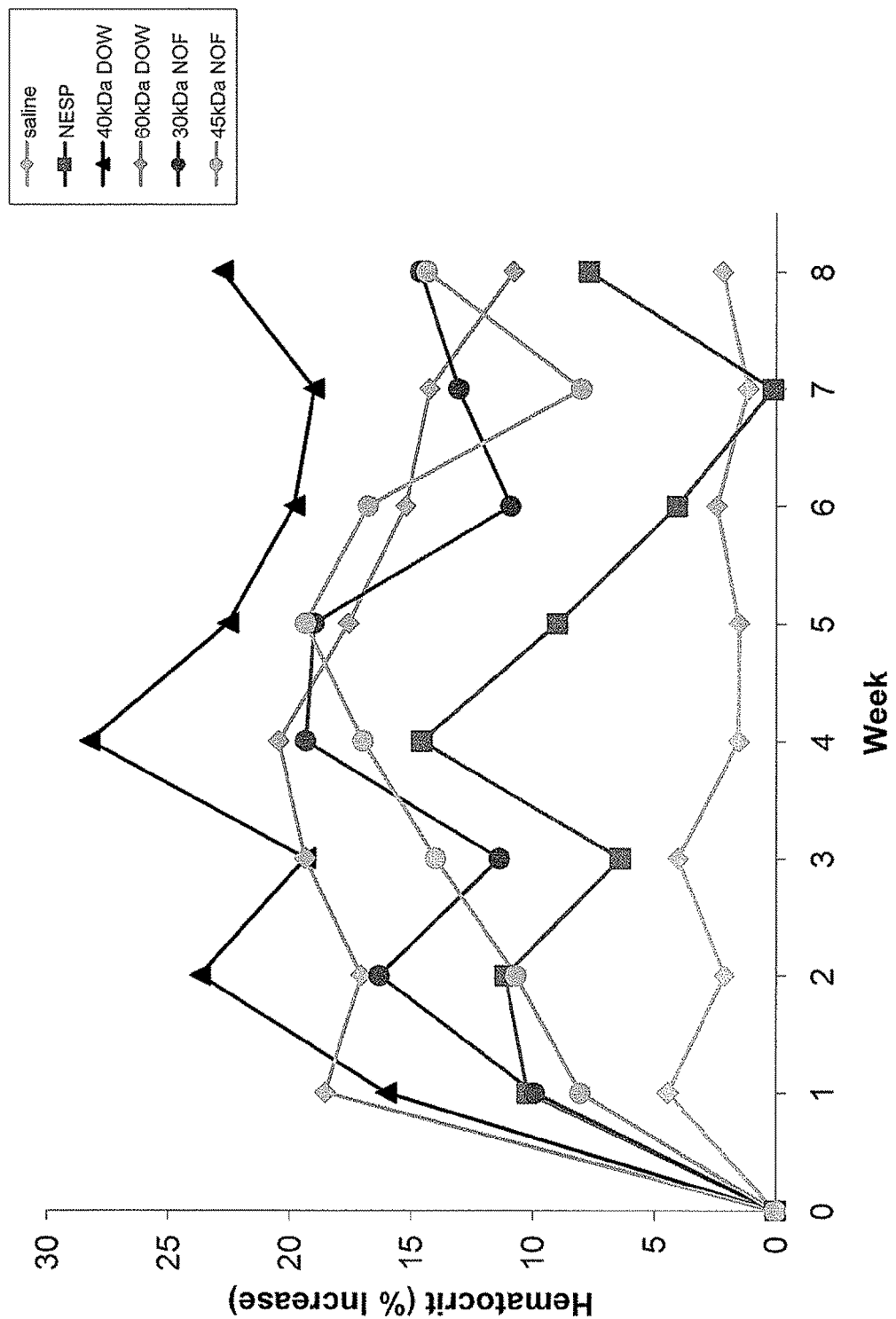
FIG. 13 shows the effect of once weekly PEG-EPO dosing on relative hematocrit increase in mice.

A second study was conducted in which the animals: C57 black mice (7 weeks of age; ~20 g; 3 males/3 females per group) were administered a single weekly 2.5 µg/kg/dose of recombinant human epo. Injections were on Thursdays and the animals were bled on Mondays during the course of the study. The study assessed the effect on hematocrit levels of once weekly intraperitoneal administration of four PEG-EPO conjugates and Aranesp (NESP). The data are presented in FIG. 13.

Immunogenicity Studies:

In order to address the immunogenic properties of PEG-EPO, rhesus monkeys can be dosed subcutaneously twice/week for 2 weeks. An ELISA-based approach can specifically identify and measure antibodies to recombinant erythropoietin in rhesus and subsequently human blood. Following subcutaneous administration of PEG-EPO, serum samples can be monitored over time for the generation of anti-erythropoietin antibodies. In addition, potential antibody responses can be correlated with pharmacokinetic and pharmacodynamic parameters that can be monitored concurrently.

SEQUENCE LISTING

<160> NUMBER OF SEQ ID NOS: 2

<210> SEQ ID NO 1
<211> LENGTH: 558
<212> TYPE: DNA
<213> ORGANISM: human

```
<400> SEQUENCE: 1
atgagatttc cttcaatttt tactgctgtt ttattcgcag catcctccgc attagctgct    60
ccaccaagat tgatttgtga ctccagagtt ttggagagat acttgttgga ggctaaagag   120
gctgagaaca tcactactgg ttgtgctgaa cactgttcct tgaacgagaa catcacagtt   180
ccagacacta aggttaactt ctacgcttgg aagagaatgg aagttggaca acaggctgtt   240
gaagtttggc aaggattggc tttgttgtcc gaggctgttt tgagaggtca agctttgttg   300
gttaactcct cccaaccatg ggaaccattg caattgcacg ttgacaaggc tgtttctgga   360
ttgagatcct tgactacttt gttgagagct ttgggtgctc agaaagaggc tatttctcca   420
ccagatgctg cttcagctgc tccattgaga actatcactg ctgacacttt cagaaagttg   480
ttcagagttt actccaactt cttgagagga aagttgaagt tgtacactgg tgaagcttgt   540
agaactggtg actagtaa                                                  558

<210> SEQ ID NO 2
<211> LENGTH: 165
<212> TYPE: PRT
<213> ORGANISM: human

<400> SEQUENCE: 2

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr G gene functions and expresses Mannosidase I, GlcNAc Transferase I, Mannosidase II, GlcNAc Transferase II, UDP galactose transporter, UDP-galactose 4-epimerase, Galactosyl Transferase, CMP-sialic acid transporter, UDP-GlcNAc 2-epimerase/N-acetylmannosamine kinase, CMP-sialic acid synthase, N-acetylneuraminate-9-phosphate synthase, and Sialyl transferase.

4. The method of claim 1, wherein greater than 50 mole percent of said plurality of N-linked glycans consists essentially of $GlcNAc_2Man_3GlcNAc_2Gal_2NANA_2$.

5. The method of claim 1, wherein greater than 75 mole percent of said plurality of N-linked glycans consists essentially of $GlcNAc_2Man_3GlcNAc_2Gal_2NANA_2$.

6. The method of claim 1, wherein said $GlcNAc_2Man_3GlcNAc_2Gal_2NANA_2$ N-glycan is present at a level from about 5 mole percent to about 80 mole percent more than the next most predominant N-linked glycan structure of said plurality of N-linked glycans.

7. The method of claim 1, wherein a polyethylene glycol moiety is linked to the N-terminal amino acid residue of at least 50% of the erythropoietin proteins, said link being an amine linkage.

8. The method of claim 7, wherein the polyethylene glycol moiety has a molecular weight of from about 20 kD to about 60 kD.

9. The method of claim 7, wherein the polyethylene glycol moiety has a molecular weight of from about 30 kD to about 40 kD.

10. The method of claim 7, wherein the polyethylene glycol moiety is linear.

\* \* \* \* \*